(12) United States Patent
Vo-Dinh et al.

(10) Patent No.: US 9,987,358 B2
(45) Date of Patent: Jun. 5, 2018

(54) NANOSTARS AND NANOCONSTRUCTS FOR DETECTION, IMAGING, AND THERAPY

(71) Applicant: Duke University, Durham, NC (US)

(72) Inventors: Tuan Vo-Dinh, Chapel Hill, NC (US); Hsiangkuo Yuan, Chalfont, PA (US); Andrew Fales, Duhanm, NC (US); Christopher Khoury, Durham, NC (US)

(73) Assignee: Duke University, Durham, NC (US)

( * ) Notice: Subject to any disclaimer, the term of this patent is extended or adjusted under 35 U.S.C. 154(b) by 0 days. days.

(21) Appl. No.: 15/408,563

(22) Filed: Jan. 18, 2017

(65) Prior Publication Data

US 2017/0151331 A1 Jun. 1, 2017

Related U.S. Application Data

(62) Division of application No. 13/971,822, filed on Aug. 20, 2013, now Pat. No. 9,561,292.

(60) Provisional application No. 61/691,858, filed on Aug. 22, 2012, provisional application No. 61/691,004, filed on Aug. 20, 2012.

(51) Int. Cl.
*A61K 41/00* (2006.01)
*A61K 49/18* (2006.01)
*G01N 33/58* (2006.01)

(52) U.S. Cl.
CPC ...... *A61K 41/0057* (2013.01); *A61K 49/1821* (2013.01); *G01N 33/582* (2013.01)

(58) Field of Classification Search
CPC .................................................. A61K 41/0057
See application file for complete search history.

(56) References Cited

U.S. PATENT DOCUMENTS

2008/0266555 A1* 10/2008 Murphy ................. B82Y 30/00
356/301
2011/0052671 A1* 3/2011 Zasadzinski ....... A61K 49/0043
424/450

OTHER PUBLICATIONS

Schütz, Hydrophilically stabilized gold nanostars as SERS labels for tissue imaging of the tumor suppressor p63 by immuno-SERS microscopy, Chem. Commun., 2011, 47, 4216-4218.*

* cited by examiner

*Primary Examiner* — Paul W Dickinson
(74) *Attorney, Agent, or Firm* — NK Patent Law, PLLC

(57) ABSTRACT

A polymer-free synthesis method is provided for preparation of monodisperse nanostars. The nanostars can be used for treating and imaging cells in in vivo or ex vivo. The modes of treatment include use of a nanostar modified with a photo-activatable drug, which drug is activated by the photo-response of the nanostar to electromagnetic stimulation; use of a nanostar modified with a thermally-activatable drug, which drug is activated by a thermal response of the nanostar to electromagnetic stimulation; and the thermal response of the nanostar itself to electromagnetic stimulation, which can directly or indirectly cause the death of an undesirable cell.

10 Claims, 18 Drawing Sheets

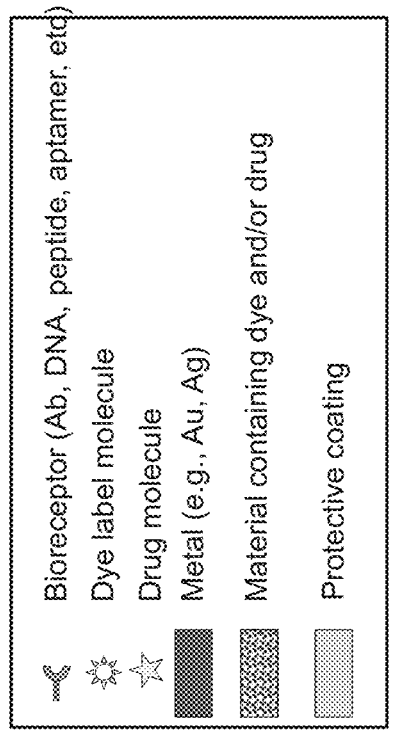
Bioreceptor (Ab, DNA, peptide, aptamer, etc)
Dye label molecule
Drug molecule
Metal (e.g., Au, Ag)
Material containing dye and/or drug
Protective coating
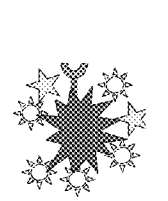
FIG. 2A
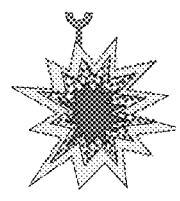
FIG. 2B
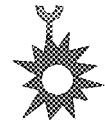
FIG. 2C
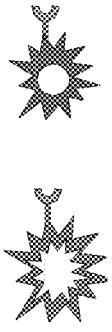
FIG. 2D
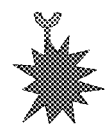
FIG. 2E
FIG. 2F
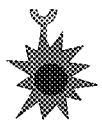
FIG. 2G  FIG. 2H
FIG. 2I

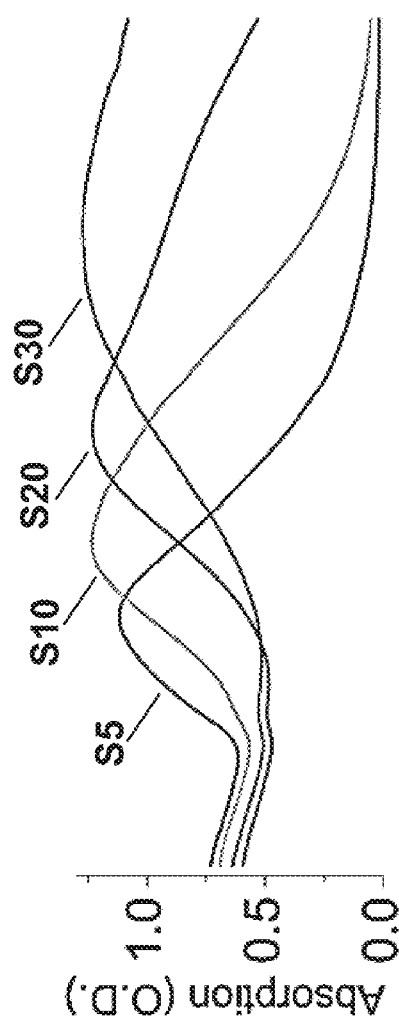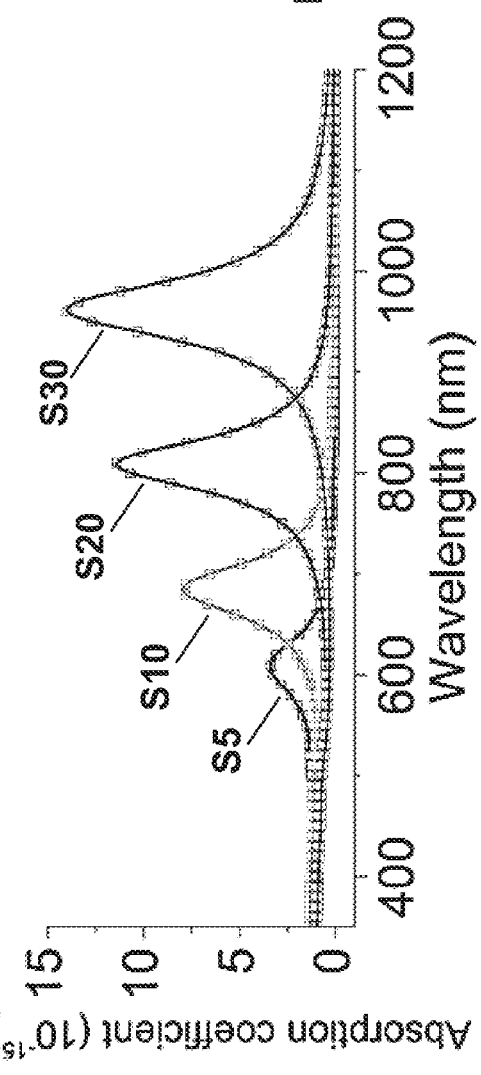
FIG. 8A
FIG. 8B

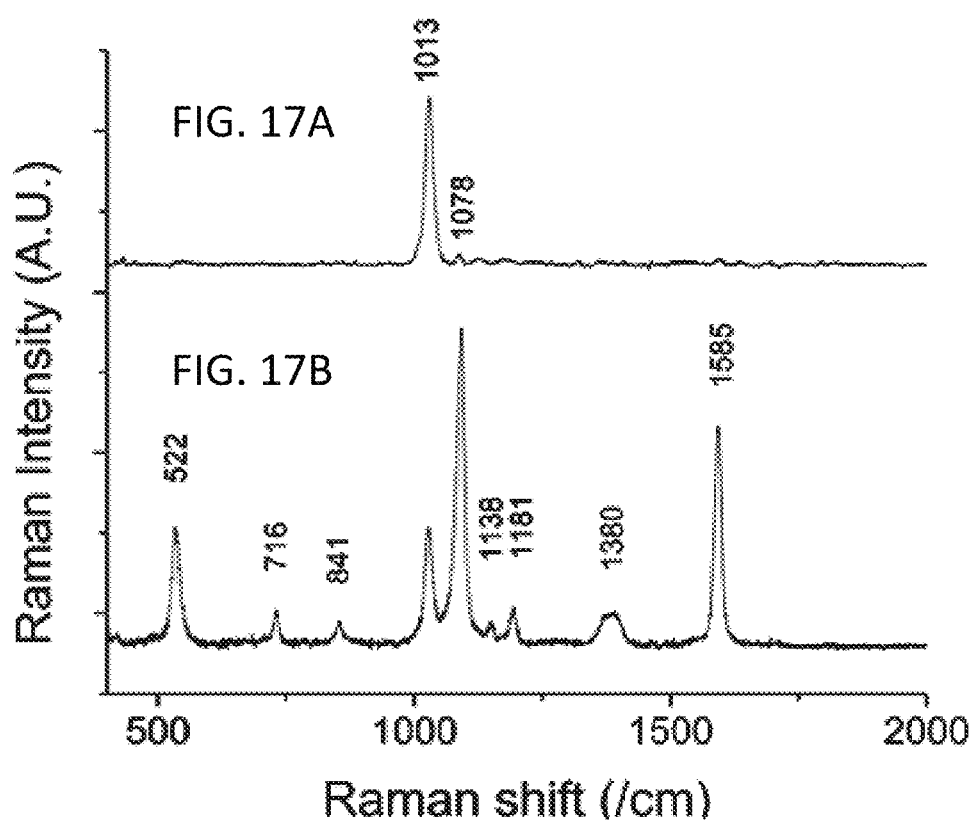

NANOSTARS AND NANOCONSTRUCTS FOR DETECTION, IMAGING, AND THERAPY

CROSS REFERENCE TO RELATED APPLICATIONS

This application is a divisional of U.S. patent application Ser. No. 13/971,822 entitled "Nanostars and Nanoconstructs for Detection, Imaging, and Therapy", filed on Aug. 20, 2013, which further claims priority to U.S. Provisional Patent Application No. 61/691,858 filed Aug. 22, 2012, and U.S. Provisional Patent Application No. 61/691,004 filed Aug. 20, 2012, the disclosures of which are incorporated herein by reference in their entirety. This application is related to U.S. patent application Ser. No. 13/888,226 filed May 6, 2013.

STATEMENT OF GOVERNMENT SUPPORT

This invention was made with U.S. Government support under the National Institutes of Health grant No's.: R01 EB006201, R01 ES014774 and T32 EB001040. The U.S. Government has certain rights in the invention.

TECHNICAL FIELD

The present disclosure relates to metal nanostars. Particularly, the present disclosure relates to methods for making and using plasmonics-active metal nanostars to treat and detect cells in vivo and ex vivo.

BACKGROUND

The development and fabrication of plasmonics-active metallic nanostructures have been active areas of research for a wide variety of applications. Plasmonics refers to the study of enhanced electromagnetic properties of metallic nanostructures. The term is derived from plasmons, the quanta associated with longitudinal waves propagating in matter through the collective motion of large numbers of electrons. According to classical electromagnetic theory, molecules on or near metal nanostructures experience enhanced fields relative to that of the incident radiation. When a metallic nanostructured surface is irradiated by an incident electromagnetic field (e.g., a laser beam), conduction electrons are displaced into frequency oscillations equal to those of the incident light. These oscillating electrons, called "surface plasmons," produce a secondary electric field, which adds to the incident field. The origin of plasmon resonances of metallic nanoparticles is collective oscillations of the conduction band electrons in the nanoparticles, which are called Localized Surface Plasmons (LSPs). LSPs can be excited when light is incident on metallic nanoparticles having a size much smaller than the wavelength of the incident light. At a suitable wavelength, resonant dipolar and multipolar modes can be excited in the nanoparticles, which lead to a significant enhancement in absorbed and scattered light and enhancement of electromagnetic fields inside and near the particles. Hence, the LSPs can be detected as resonance peaks in the absorption or scattering spectra of the metallic nanoparticles. This condition yields intense localized fields, which can interact with molecules in contact with or near the metal surface. In an effect analogous to a "lightning rod" effect, secondary fields can become concentrated at high curvature points on the nanostructured metal surface.

Nanoparticles of noble metals such as gold and silver resonantly scatter and absorb light in the visible and near-infrared spectral region upon the excitation of their plasmon and are therefore materials of choice for plasmon related devices. Surface plasmons have been associated with important practical applications in surface plasmon resonance (SPR), surface-enhanced Raman scattering (SERS) and surface-enhanced luminescence, also referred to as metal-enhanced luminescence. Such SERS technology has been extensively investigated and a wide variety of plasmonics-active SERS platforms developed for chemical sensing and for bioanalysis and biosensing [T. Vo-Dinh, "Surface-Enhanced Raman Spectroscopy Using Metallic Nanostructures," Trends in Anal. Chem., 17, 557-582 (1998); T. Vo-Dinh, A. Dhawan, S. J. Norton, C. G. Khoury, H-N. Wang, V. Misra, and M. Gerhold "Plasmonic Nanoparticles and Nanowires: Design, Fabrication and Application in Sensing", J. Phys. Chem. C, 114 (16), pp 7480-7488 (2010).

Photodynamic Therapy (PDT) is light-based treatment, which involves treatment of diseases such as cancer using light action on a special photoactive class of drugs, by photodynamic action in vivo to destroy or modify tissue [Dougherty T. J. and Levy J. G., "Photodynamic Therapy and Clinical Applications", in Biomedical Photonics Handbook, Vo-Dinh T., Ed., CRC Press, Boca Raton Fla. (2003)]. PDT, which was originally developed for treatment of various cancers, has now been used to include treatment of pre-cancerous conditions, e.g. actinic keratoses, high-grade dysplasia in Barrett's esophagus, and non-cancerous conditions, e.g. various eye diseases, e.g. age related macular degeneration. Photodynamic therapy (PDT) is approved for commercialization worldwide both for various cancers (lung, esophagus) and for AMD. The PDT process requires three elements: (1) photosensitizer), (2) light that can excite the photosensitizer (Ps) and (3) endogenous oxygen. The putative cytotoxic agent is singlet oxygen, an electronically excited state of ground state triplet oxygen formed according to Type II photochemical process.

Transition to the triplet state is important since the triplet state has a relatively long lifetime (μsec to seconds). As a result photosensitizers that undergo efficient intersystem crossing to the excited triplet state will have sufficient time for collision with oxygen in order to produce singlet oxygen. The energy difference between ground state and singlet oxygen is 94.2 kJ/mol and corresponds to a transition in the near-infrared (NIR) at ~1270 nm. Most PS photosensitizers in clinical use have triplet quantum yields in the range of 40-60% with the singlet oxygen yield being slightly lower. Competing processes include loss of energy by deactivation to ground state by fluorescence or internal conversion (loss of energy to the environment).

Many factors, including a high yield of singlet oxygen, pharmacokinetics, pharmacodynamics, stability in vivo and acceptable toxicity, play critical roles as well [Henderson B W, Gollnick S O, "Mechanistic Principles of Photodynamic Therapy", in Biomedical Photonics Handbook, Vo-Dinh T., Ed., CRC Press, Boca Raton Fla. (2003)]. For example, it is desirable to have relatively selective uptake in the tumor or other tissue being treated relative to the normal tissue that necessarily will be exposed to the exciting light as well. Pharmacodynamic issues such as the subcellular localization of the photosensitizer may be important as certain organelles appear to be more sensitive to PDT damage than others (e.g. the mitochondria). Toxicity can become an issue if high doses of photosensitizer are necessary in order to obtain a complete response to treatment. An important mechanism associated with PDT drug activity involves apoptosis in cells. Upon absorption of light, the photosensitiser (Ps) initiates chemical reactions that lead to the direct or indirect production of cytotoxic species such as radicals and singlet oxygen. The reaction of the cytotoxic species with subcellular organelles and macromolecules (proteins, DNA, etc) lead to apoptosis and/or necrosis of the cells hosting the PDT drug. The preferential accumulation of PDT drug molecules in cancer cells combined with the localized delivery of light to the tumor, results in the selective destruction of the cancerous lesion. Compared to other traditional anticancer therapies, PDT does not involve generalized destruction of healthy cells. In addition to direct cell killing, PDT can also act on the vasculature, reducing blood flow to the tumor causing its necrosis. In particular cases it can be used as a less invasive alternative to surgery.

There are several chemical species used for PDT including porphyrin-based sensitizers. A purified hematoporphyrin derivative, Photofrin®, has received approval of the US Food and Drug Administration. Porphyrins are generally used for tumors on or just under the skin or on the lining of internal organs or cavities because theses drug molecules absorb light shorter than 640 nm in wavelength. For tumors occurring deep in tissue, second generation sensitizers, which have absorbance in the NIR region, such as porphyrin-based systems [R. K. Pandey, "*Synthetic Strategies in designing Porphyrin-Based Photosensitizers*", in *Biomedical Photonics Handbook*, Vo-Dinh T., Ed., CRC Press, Boca Raton Fla. (2003)], chlorines, phthalocyanine, and naphthalocyanine have been investigated.

Nanoparticle systems have gained wide attention due to their potential in medicine, such as molecular imaging, immunization, theranostics, and targeted delivery/therapy. Nanoparticles can be fabricated as strong contrast agents for different imaging modalities with superior signal-to-noise ratios than conventional agents, or as therapeutic agents such as drug carriers, radioenhancers, and photothermal transducers. Gold nanoparticles (AuNPs), with their facile synthesis and biocompatibility, have therefore been applied for a variety of therapeutics, especially in cancer therapy.

These substrates consist of microplates, waveguides or optical fibers having silver-coated dielectric nanoparticles or isolated dielectric nanospheres coated with a silver nanolayer producing nanocaps (i.e. half nanoshells), nanorods and nanostars. These plasmonics substrate platforms have led to a wide variety of analytical applications including sensitive detection of a variety of chemicals of environmental, biological and medical significance, including polycyclic aromatic compounds, organophosphorus compounds, and compounds of biological interest such as DNA-adduct biomarkers.

Gold nanostars (NS), with a high absorption-to-scattering ratio in the NIR, efficiently transduce photon energy into heat for hyperthermia therapy. To date, most phothermolysis studies utilize laser irradiation higher than the maximal permissible exposure (MPE) of skin by ANSI regulation. To make photothermolysis applicable to real practice, one needs to enhance the photothermal transduction efficiency. One way is to use a pulsed laser instead of a continuous-wave laser, permitting efficient photothermal conversion by allowing additional time for electron-phonon relaxation. Previously, in vitro photothermolysis using NIR pulsed laser reported irradiances of 1.6-48.6 $W/cm^2$; which were higher than the MPE of skin (e.g. 0.4 $W/cm^2$ at 800 nm). Insufficient intracellular particle delivery and low photothermal transduction efficiency may be the main obstacles. Therefore, there is a strong need to design a more efficient photothermal transducer with optimized cellular uptake.

Recently, star-shaped AuNPs ("nanostars") have attracted interest because their plasmon can be tuned to the NIR region, and the structure contains multiple sharp tips that can greatly enhance incident electromagnetic fields. Studies have shown that NIR-absorbing nanorods, nanocages or nanoshells can be used as contrast agents in optical imaging techniques such as optical coherent tomography, two-photon luminescence (TPL) microscopy, and photoacoustic imaging. Their large absorption cross-sections can also effectively convert photon energy to heat during photothermal therapy. Nanostars, which absorb in the NIR, have been hypothesized to behave similarly. Nanostar-related bioapplications remain scarce in spite of their potential, mostly due to the difficulty of surface functionalization.

In 2003, Chen et al. [Chen S, Wang Z L, BaHato J, Foulger S H, Carroll D L., *J Am Chem Soc.* 2003 Dec. 31; 125(52):16186-7] first reported the synthesis of multipod gold nanoparticles from silver plates in the presence of cetyltrimethylammonium bromide (CTAB) and NaOH. Later, several seedless or seed-mediated synthesis methods were employed using majorly poly(N-vinylpyrolidone) (PVP) or CTAB as surfactant. Further use of nanostars has been limited by (1) the potential toxicity of CTAB, (2) the difficulty of replacing PVP or CTAB during biofunctionalization, and (3) induction of aggregation following multiple washes. Previous experimental studies have shown a red-shifting of the plasmon peak from nanostars with longer or sharper branches. Several numerical studies of their plasmonic properties have recently been reported. Hao et al.'s [Hao F, Nehl C L, Hafner J H, Nordlander P. *Nano Lett.* 2007 March; 7(3):729-32] 2-D modeling of a single nanostar, consisting of 5 unique branches, with finite difference time domain (FDTD) method showed that nanostars plasmon results from the hybridization of plasmon resonance of each branch; the plasmon peak relative intensity depends on the polarization angle. Senthil et al. [Senthil Kumar P, Pastoriza-Santos I, Rodríguez-Ganzález B, Garcia de Abajo F J, Liz-Marzán L M. *Nanotechnology,* 2008; 19(1):015606-12] also stated that the tip angle and radius, but not the number of branches, are the major determining factors in plasmon shift in a simplistic 2-branch model.

Because existing nanoparticles are associated with limitations as described above, new nanoparticles with improved properties are therefore desirable.

SUMMARY OF THE INVENTION

In one embodiment, a plasmonics-active gold nanostar is provided resulting from a process comprising: reducing aqueous gold ($Au^{3+}$) to solid gold (Au) in an acidic solution; and mixing a silver salt compound with a weak reducing agent into the solution under conditions such that the plasmonics-active gold nanostars are produced.

In one embodiment, a method is provided for preparing plasmonics-active gold nanostars free of polymer, the method comprising: reducing aqueous gold ($Au^{3+}$) to solid gold (Au) in an acidic solution; and mixing a silver salt compound with a weak reducing agent into the solution under conditions such that the plasmonics-active gold nanostars are produced.

In one embodiment, a method is provided of treating undesirable cells comprising: contacting an undesirable cell with a plasmonics-active gold nanostar resulting from a process comprising: reducing aqueous gold ($Au^{3+}$) to solid gold (Au) in an acidic solution; and mixing a silver salt compound with a weak reducing agent into the solution under conditions such that the plasmonics-active gold nanostars are produced; and applying a single-photon or multi-photon excitation to the undesirable cells such that the undesirable cells are damaged by one or both of thermal energy from the single-photon or multi-photon excitation and thermal energy emitted as a result of excitation of the nanostar by the single-photon or multi-photon excitation.

In one embodiment, a method is provided wherein the plasmonics-active gold nanostar further comprises one or more of a photosensitizer and a photoactivator, wherein the photosensitizer and the photoactivator absorb electromagnetic radiation from one or both of electromagnetic radiation emitted as a result of excitation of the nanostar and directly from the single-photon or multi-photon excitation, such that the undesirable cells are damaged by one or a combination of thermal energy from the single-photon or multi-photon excitation, thermal energy emitted by the nanostar, reactive oxygen species (ROS) generated by the photosensiter, and one or a combination of activation and release of the photoactivator.

BRIEF DESCRIPTION OF THE DRAWINGS

The foregoing summary, as well as the following detailed description of various embodiments, is better understood when read in conjunction with the appended figures. For the purposes of illustration, there is shown in the Figures exemplary embodiments; however, the presently disclosed subject matter is not limited to the specific methods and exemplary embodiments disclosed.

FIGS. 2A-2I are schematic diagrams showing a series of plasmonics-active nanostars with bioreceptor according to one or more embodiments of the present disclosure. 2A-2H show the plasmonics-active nanostars and 2I shows the legend.

FIGS. 8A-8B are absorbance spectra illustrating the tunability of the nanostars' plasmon peak from 600 nm to 1000 nm according to one or more embodiments of the present disclosure. (A) Absorbance spectra (unnormalized) of the star solutions (~0.2 nM) in citrate buffer. (inset) Photograph of the corresponding star solutions. (B) Corresponding FEM-generated absorption spectra (±1 SD) of nanostars embedded in water. The solved data points were interpolated with a spline fit. The orientation dependence of the incident E-field was accounted for by averaging the absorption spectra of the nanostars as they were incrementally rotated by 30 degrees in the [x=y] plane, such that the orientation of the branches relative to the z-polarized incident field became randomized.

FIGS. 17A-17B are SERS spectra of 4-MBA (1 μM) on 0.1 nM nanospheres A) and nanostars B) examined under 785 nm and 633 nm excitations according to one or more embodiments of the present disclosure. 10% v/v methanol was used as an internal reference.

DETAILED DESCRIPTION OF THE INVENTION

Figure 1A:
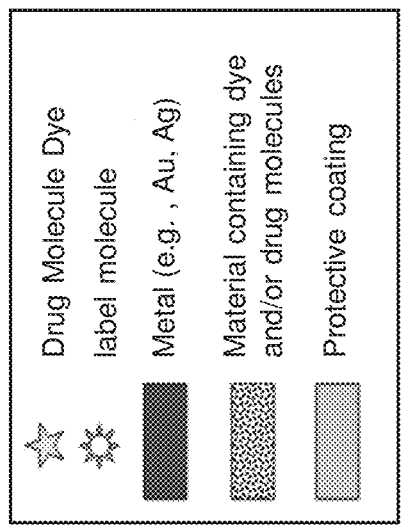
FIGS. 1A-1I are schematic diagrams showing a series of plasmonics-active nanostars according to one or more embodiments of the present disclosure. 1A-1H show the plasmonics-active nanostars and 1I shows the legend.

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "a cell" means at least one cell and can include a number of cells.

Unless otherwise defined, all technical terms used herein have the same meaning as commonly understood by one of ordinary skill in the art to which this disclosure belongs.

As used herein, the term "nanostar" or "NS" means a nanoparticle which has a single core section with two or more protrusions emitting from the core section of the nanoparticle. These protrusions are usually conical or pyramidal in form, but not always.

The present disclosure is provided in response to a need to develop a versatile platform for use in diagnostics, imaging and disease treatment. In addition, there is also a need for a combination of both diagnostics and therapy, and the present disclosure provides a solution referred to herein as "theranostics". The subject matter disclosed herein describes fabrication and application of plasmonics-active metallic platforms such as nanostars for various theranostics applications combining and including, but not limited to: Surface-enhanced Raman scattering (SERS) diagnostics and imaging; Enhanced fluorescence detection using single and two-photon excitation; Enhanced diffuse scattering diagnostics and imaging; Enhanced optical coherence tomography (OCT); Enhanced photoacoustics; Enhanced photothermal therapy; Enhanced photodynamic therapy; Enhanced immunotherapy; and Enhanced theranostics by combining the above detection modalities (diagnostics) with therapy modalities.

Enhancement mechanisms of the electromagnetic field effect that can increase the absorption of the excitation light used for optical diagnostics and therapy is the basic mechanism of the NIDT operating principle. There are two main sources of electromagnetic enhancement: (1) first, the laser electromagnetic field is enhanced due to the addition of a field caused by the polarization of the metal particle; (2) in addition to the enhancement of the excitation laser field, there is also another enhancement due to the molecule radiating an amplified emission (luminescence, Raman, etc.) field, which further polarizes the metal particle, thereby acting as an antenna to further amplify the Raman/Luminescence signal.

Electromagnetic enhancements are divided into two main classes: a) enhancements that occur only in the presence of a radiation field, and b) enhancements that occur even without a radiation field. The first class of enhancements is further divided into several processes. Plasma resonances on the substrate surfaces, also called surface plasmons, provide a major contribution to electromagnetic enhancement. An effective type of plasmonics-active substrate consists of nanostructured metal particles, protrusions, or rough surfaces of metallic materials. Incident light irradiating these surfaces excites conduction electrons in the metal, and induces excitation of surface plasmons leading to Raman/Luminescence enhancement. At the plasmon frequency, the metal nanoparticles (or nanostructured roughness) become polarized, resulting in large field-induced polarizations and thus large local fields on the surface. These local fields increase the Luminescence/Raman emission intensity, which is proportional to the square of the applied field at the molecule. As a result, the effective electromagnetic field experienced by the analyte molecule on theses surfaces is much larger than the actual applied field. This field decreases as $1/r^3$ away from the surface. Therefore, in the electromagnetic models, the luminescence/Raman-active analyte molecule is not required to be in contact with the metallic surface but can be located anywhere within the range of the enhanced local field, which can polarize this molecule. The dipole oscillating at the wavelength $\lambda$ of Raman or luminescence can, in turn, polarize the metallic nanostructures and, if $\lambda$ is in resonance with the localized surface plasmons, the nanostructures can enhance the observed emission light (Raman or luminescence). There are two main sources of electromagnetic enhancement: (1) first, the laser electromagnetic field is enhanced due to the addition of a field caused by the polarization of the metal particle; (2) in addition to the enhancement of the excitation laser field, there is also another enhancement due to the molecule radiating an amplified Raman/Luminescence field, which further polarizes the metal particle, thereby acting as an antenna to further amplify the Raman/Luminescence signal. Plasmonics-active metal nanoparticles also exhibit strongly enhanced visible and near-infrared light absorption, several orders of magnitude more intense compared to conventional laser phototherapy agents. The use of plasmonic nanoparticles as highly enhanced photoabsorbing agents has thus introduced a much more selective and efficient phototherapy strategy. The tunability of the spectral properties of the metal nanoparticles and the biotargeting abilities of the plasmonic nanostructures make the method desireable.

The methods and compositions of the present disclosure are based on several important mechanisms: Increased absorption of the excitation light by the plasmonic metal nanoplatforms (i.e., nanostars) resulting in enhanced absorption of the nanoplatforms; Increased absorption of the excitation light by the plasmonic metal nanoplatforms (i.e., nanostars), yielding more light for excitation of optical labels (Raman, fluorescence, etc); Increased absorption of the excitation light by the plasmonic metal nanoplatforms (i.e., nanostars), resulting in increased photothermal heating of the plasmonic metal nanoplatforms (i.e., nanostars); Increased absorption of the excitation light by the dye (Raman, fluorescent, phosphorescent labels, etc) adsorbed on or near the plasmonic metal nanoplatforms (i.e., nanostars); Increased light absorption of the dye label molecules adsorbed on or near the metal nanoplatforms (i.e., nanostars); Amplified emission from the dye label and/or photodynamic molecules adsorbed on or near the metal nanoparticles; and Combination of enhanced detection and enhanced therapy via the above processes.

One of several phenomena that can enhance the efficiency of light emitted (Raman or luminescence) from molecules adsorbed or near a metal nanostructures Raman scatter is the SERS effect discovered in the 1970s [Fleischmann; Hendra, P. J.; McQuillan A. *J. Chem. Phys. Lett.* 1974, 26 (2), 163-166; Jeanmaire, D. L.; Vanduyne, R. P. *J. Electroanal. Chem.* 1977, 84 (1), 1-20; Albrecht, M. G.; Creighton, J. A. *J. Am. Chem. Soc.* 1977, 99 (15), 5215-5217]. In 1984, the Vo-Dinh's laboratory first reported the general applicability of SERS as an analytical technique, and the possibility of SERS measurement for a variety of chemicals including several homocyclic and heterocyclic polyaromatic compounds [T. Vo-Dinh, M. Y. K. Hiromoto, G. M. Begun and R. L. Moody, "*Surface-enhanced Raman spectroscopy for trace organic analysis,*" *Anal. Chem.*, vol. 56, 1667, 1984]. Extensive research has been devoted to understanding and modeling the Raman enhancement in SERS since the mid 1980's. The intensity of the normally weak Raman scattering process is increased by factors as large as $10^{13}$ or $10^{15}$ for compounds adsorbed onto "hot spots" on a plasmonics-active substrate, allowing for single-molecule detection. As a result of the electromagnetic field enhancements produced near nanostructured metal surfaces, nanoparticles have found increased use as fluorescence and Raman nanoprobes.

The theoretical models indicate that it is possible to tune the size of the nanoparticles and the nanoshells to the excitation wavelength. Experimental evidence suggests that the origin of the $10^6$- to $10^{15}$-fold Raman enhancement primarily arises from two mechanisms: a) an electromagnetic "lightning rod" effect occurring near metal surface structures associated with large local fields caused by electromagnetic resonances, often referred to as "surface plasmons"; and b) a chemical effect associated with direct energy transfer between the molecule and the metal surface.

According to classical electromagnetic theory, electromagnetic fields can be locally amplified when light is incident on metal nanostructures. These field enhancements can be quite large (typically $10^6$- to $10^7$-fold, but up to $10^{15}$-fold enhancement at "hot spots"). When a nanostructured metallic surface is irradiated by an electromagnetic field (e.g., a laser beam), electrons within the conduction band begin to oscillate at a frequency equal to that of the incident light. These oscillating electrons, called "surface plasmons," produce a secondary electric field, which adds to the incident field. If these oscillating electrons are spatially confined, as is the case for isolated metallic nano spheres or roughened metallic surfaces (nanostructures), there is a characteristic frequency (the plasmon frequency) at which there is a resonant response of the collective oscillations to the incident field. This condition yields intense localized field enhancements that can interact with molecules on or near the metal surface. In an effect analogous to a "lightning rod," secondary fields are typically most concentrated at points of high curvature on the roughened metal surface.

Figure 1B:
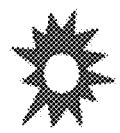
Figure 1C:
Figure 1D:
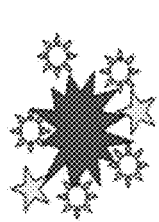
Figure 1E:
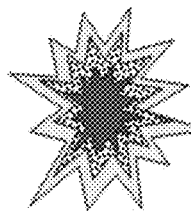
Figure 1F:
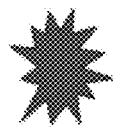
Figure 1G:
Figure 1H:
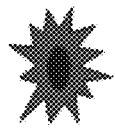
Figure 1I:
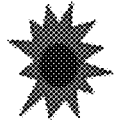

FIGS. 1A-1H are schematic diagrams showing various plasmonics-active nanostars according to one or more embodiments of the present disclosure. FIG. 1I shows the legend for FIGS. 1A-1H. FIG. 1A shows a plasmonics-active nanostar. FIG. 1B shows the nanostar labeled with optical dye and/or a drug molecule. FIG. 1C shows the nanostar having a layer embedded with a label and/or a drug. FIG. 1D shows the nanostar with a layer embedded with a label and/or drug and a protective overlayer. FIG. 1E shows the nanostar with a paramagnetic spherical nucleus. FIG. 1F shows the nanostar with an elongated paramagnetic nucleus. FIG. 1G shows the nanostar having a void-space. FIG. 1H shows the nanostar having an empty or dielectric core.

In another aspect of the present disclosure, the nanostars can include bioreceptors that can be used for specificity for targeting disease cells. The bioreceptors can be responsible for binding the nanostar to the biotarget of interest for therapy. These bioreceptors can take many forms and the different bioreceptors that can be used are as numerous as the different analytes that have been monitored using biosensors. Bioreceptors can generally be classified into five different major categories. These categories include: 1) antibody/antigen, 2) enzymes, 3) nucleic acids/DNA, 4) cellular structures/cells and 5) biomimetic (aptamers, peptides, etc).

FIGS. 2A-2H are schematic diagrams showing various plasmonics-active nanostars with bioreceptor according to one or more embodiments of the present disclosure. FIG. 2I shows the legend for FIGS. 2A-2H. The nanostars shown in FIGS. 2A-2H are similar to those shown in FIGS. 6A-H but also have a bioreceptor for targeting to a specific cell or a tumor. FIG. 2A shows a plasmonics-active nanostar with bioreceptor. FIG. 2B shows the nanostar labeled with optical dye and/or a drug molecule with bioreceptor. FIG. 2C shows the nanostar having a layer embedded with a label and/or a drug (e.g., psoralen) with bioreceptor. FIG. 2D shows the nanostar with a layer embedded with a label and/or drug (e.g., psoralen) and a protective overlayer with bioreceptor. FIG. 2E shows the nanostar with a paramagnetic spherical nucleus with bioreceptor. FIG. 2F shows the nanostar with an elongated paramagnetic nucleus with bioreceptor. FIG. 2G shows the nanostar having a void-space with bioreceptor. FIG. 2H shows the nanostar having an empty or dielectric core with bioreceptor.

To specifically target diseases cells, specific genes or protein markers, the nanostars of the present disclosure can be bound to a bioreceptor (e.g., antibody, DNA, proteins, cell-surface receptors, aptamers, etc.) as described above. A general description of certain of the bioreceptors is provided below.

DNA Probes.

The operation of gene probes is based on the hybridization process. Hybridization involves the joining of a single strand of nucleic acid with a complementary probe sequence. Hybridization of a nucleic acid probe to DNA biotargets (e.g., gene sequences of a mutation, etc) offers a very high degree of accuracy for identifying DNA sequences complementary to that of the probe. Biologically active DNA probes can be directly or indirectly immobilized onto a drug system, such as the EEC system (e.g., gold nanoparticle, a semiconductor, quantum dot, a glass/quartz nanoparticles, etc.) surface to ensure optimal contact and maximum binding. When immobilized onto nanoparticles including nanostars, the gene probes are stabilized and, therefore, can be reused repetitively. Several methods can be used to bind DNA to different supports. The method commonly used for binding DNA to glass involves silanization of the glass surface followed by activation with carbodiimide or glutaraldehyde. The silanization method can be used for binding to glass surfaces using 3-glycidoxypropyltrimethoxysilane (GOP) or aminopropyltrimethoxysilane (APTS) to covalently link DNA via amino linkers incorporated either at the 3' or 5' end of the molecule during DNA synthesis.

Antibody Probes.

Antibodies are biological molecules that exhibit very specific binding capabilities for specific structures and that can be used as bioreceptors. This unique property of antibodies is the key to their usefulness in immunosensors where only the specific analyte of interest, the antigen, fits into the antibody binding site.

Enzyme Probes.

Enzymes are often chosen as bioreceptors based on their specific binding capabilities as well as their catalytic activity. In biocatalytic recognition mechanisms, the detection is amplified by a reaction catalyzed by macromolecules called biocatalysts. The catalytic activity provided by enzymes allows for much lower limits of detection than would be obtained with common binding techniques. Enzyme-coupled receptors can also be used to modify recognition mechanisms.

Other Approaches.

Methods for conjugation of nanostars with receptor-binding molecules can be used that can selectively increase the adherence or uptake of nanostars for targeting cells. In addition to bioreceptor molecules such as antibodies, antibody fragments, and DNA/RNA aptamers, peptides can also be used since they offer several advantages as bioreceptors for nanostars (low cost, high activity per unit, excellent stability, long-term storage and easy handling). An enzyme-mediated process can also be used for targeting. Overexpression of certain enzymes at the site of disease can be used for the development of enzyme-responsive nanoplatforms diagnosis. For in vivo models, it is also important keep the nanoparticles out of the blood circulation to prevent clearance. The concept of using iron oxide-gold core-shell particles, can provide a unique solution. The gold shell will allow for the same functionalization methods to be used from the ex vivo work, while the iron oxide core will be superparamagnetic. A magnet can be used to collect and keep the particles at one location in the body, at which the analysis can be performed. The iron oxide core can provide for multimodality diagnostics (SERS, luminescence, MRI) and co-registration.

Bioreceptors (and other biomolecules) as well as drug molecules can be immobilized to a solid support such as a metal nanostar using a wide variety of methods published in the literature. Binding can be performed through covalent bonds by taking advantage of reactive groups such as amine ($-NH_2$) or sulfide ($-SH$) that are naturally present or can be incorporated into the bioreceptor/biomolecule structure. For example, amines can react with carboxylic acid or ester moieties in high yield to form stable amide bonds. Thiols can participate in maleimide coupling, yielding stable dialkyl-sulfides.

A solid support of interest is gold (or silver) nanoparticles. The majority of immobilization schemes involving Au(Ag) surfaces utilize a prior derivatization of the surface with alkylthiols, forming stable linkages. Alkylthiols readily form self-assembled monolayers (SAM) onto silver surfaces in micromolar concentrations. The terminus of the alkylthiol chain can be used to bind biomolecules, or can be easily modified to do so. The length of the alkylthiol chain has been found to be an important parameter, keeping the biomolecules away from the surface. Furthermore, to avoid direct, non-specific DNA adsorption onto the surface, alkylthiols have been used to block further access to the surface, allowing only covalent immobilization through the linker [Steel, A. B.; Herne, T. M.; Tarlov, M. J. Anal. Chem. 1998, 70, 4670-7; Herne, T. M.; Tarlov, M. J. J. Am. Chem. Soc. 1997, 119, 8916-20].

Silver surfaces have been found to exhibit controlled self-assembly kinetics when exposed to dilute ethanolic solutions of alkylthiols. The tilt angle formed between the surface and the hydrocarbon tail ranges from 0 to 15°. There is also a larger thiol packing density on silver, when compared to gold [Burges, J. D.; Hawkridge, F. M. Langmuir 1997, 13, 3781-6]. After SAM formation on gold/silver nanoparticles, alkylthiols can be covalently coupled to biomolecules. The majority of synthetic techniques for the covalent immobilization of biomolecules utilize free amine groups of a polypeptide (enzymes, antibodies, antigens, etc) or of amino-labeled DNA strands, to react with a carboxylic acid moiety forming amide bonds. As a general rule, a more active intermediate (labile ester) is first formed with the carboxylic acid moiety and in a later stage reacted with the free amine, increasing the coupling yield. Successful coupling procedures include:

Binding Procedure Using N-Hydroxysuccinimide (NHS) and its Derivatives.

The coupling approach involves the esterification under mild conditions of a carboxylic acid with a labile group, an N-hydroxysuccinimide (NHS) derivative, and further reaction with free amine groups in a polypeptide (enzymes, antibodies, antigens, etc) or amine-labeled DNA, producing a stable amide [Boncheva, M.; Scheibler, L.; Lincoln, P.; Vogel, H.; Akerman, B. Langmuir 1999, 15, 4317-20]. NHS reacts almost exclusively with primary amine groups. Covalent immobilization can be achieved in as little as 30 minutes. Since $H_2O$ competes with $-NH_2$ in reactions involving these very labile esters, it is important to consider the hydrolysis kinetics of the available esters used in this type of coupling. The derivative of NHS used in FIG. 1, O—(N-succinimidyl)-N,N,N',N'-tetramethyluronium tetra-fluoroborate, increases the coupling yield by utilizing a leaving group that is converted to urea during the carboxylic acid activation, hence favorably increasing the negative enthalpy of the reaction.

Binding Procedure Using Maleimide.

Maleimide can be used to immobilize biomolecules through available thiol moieties. Coupling schemes with maleimide have been proven useful for the site-specific immobilization of antibodies, Fab fragments, peptides, and SH-modified DNA strands. Sample preparation for the maleimide coupling of a protein involves the simple reduction of disulfide bonds between two cysteine residues with a mild reducing agent, such as dithiothreitol, 2-mercaptoethanol or tris(2-carboxyethyl)phosphine hydrochloride. However, disulfide reduction will usually lead to the protein losing its natural conformation, and might impair enzymatic activity or antibody recognition. The modification of primary amine groups with 2-iminothiolane hydrochloride (Traut's reagent) to introduce sulfydryl thiol groups is an alternative for biomolecules lacking them. Free sulfhydryl thiols are immobilized to the maleimide surface by an addition reaction to unsaturated carbon-carbon bonds [Jordan, C. E., et al., 1997].

Binding Procedure Using Carbodiimide.

Surfaces modified with mercaptoalkyldiols can be activated with 1,1'-carbonyldiimidazole (CDI) to form a carbonylimidazole intermediate. A biomolecule with an available amine group displaces the imidazole to form a carbamate linkage to the alkylthiol tethered to the surface [Potyrailo, R. A., et al., 1998].

Figure 3:
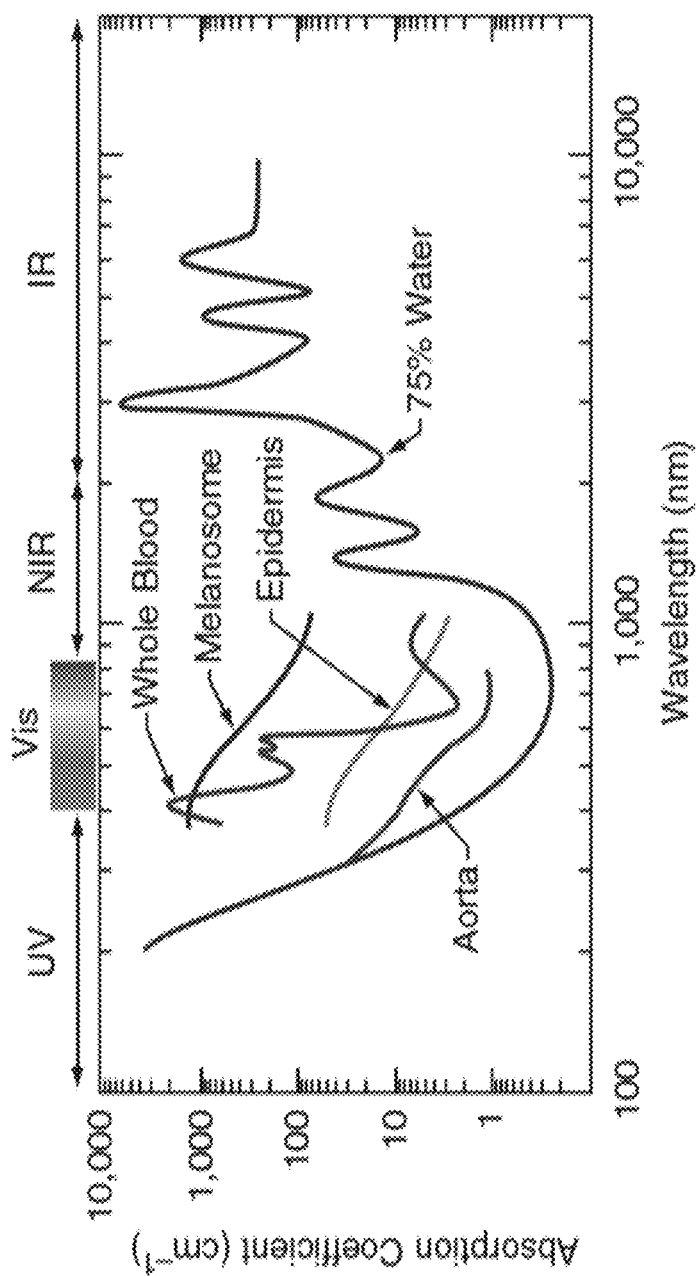
FIG. 3 is graph showing the "theranostics window" in tissue and absorption spectra of biological components.

Non-Invasive Photon Excitation Modalities of Nanostars in the NIR "Theranostic Window". *Photon Excitation in the Therapeutic Window of Tissue.* There are several methods of using light having wavelengths within the so-called "diagnostic window" or "therapeutic window" (700-1300 nm) to excite and photoactivate compounds in tissue in a non-invasive manner. Since nanostars can be used as platforms for both diagnostic and therapy, this spectral region is referred to herein as "theranostic window". The ability of light to penetrate tissues depends on absorption. Within the spectral range known as the therapeutic window (or diagnostic window), most tissues are sufficiently weak absorbers to permit significant penetration of light. This window extends from 600 to 1300 nm, from the orange/red region of the visible spectrum into the NIR. At the short-wavelength end, the window is bound by the absorption of hemoglobin, in both its oxygenated and deoxygenated forms. The absorption of oxygenated hemoglobin increases approximately two orders of magnitude as the wavelength shortens in the region around 600 nm. At shorter wavelengths many more absorbing biomolecules become important, including DNA and the amino acids tryptophan and tyrosine. At the infrared (IR) end of the window, penetration is limited by the absorption properties of water. Within the therapeutic window, scattering is dominant over absorption, and so the propagating light becomes diffuse, although not necessarily entering into the diffusion limit. FIG. 3 shows a diagram of the therapeutic window of tissue. The following section discusses the use of one-photon and multi-photon techniques for therapy.

Figure 4:
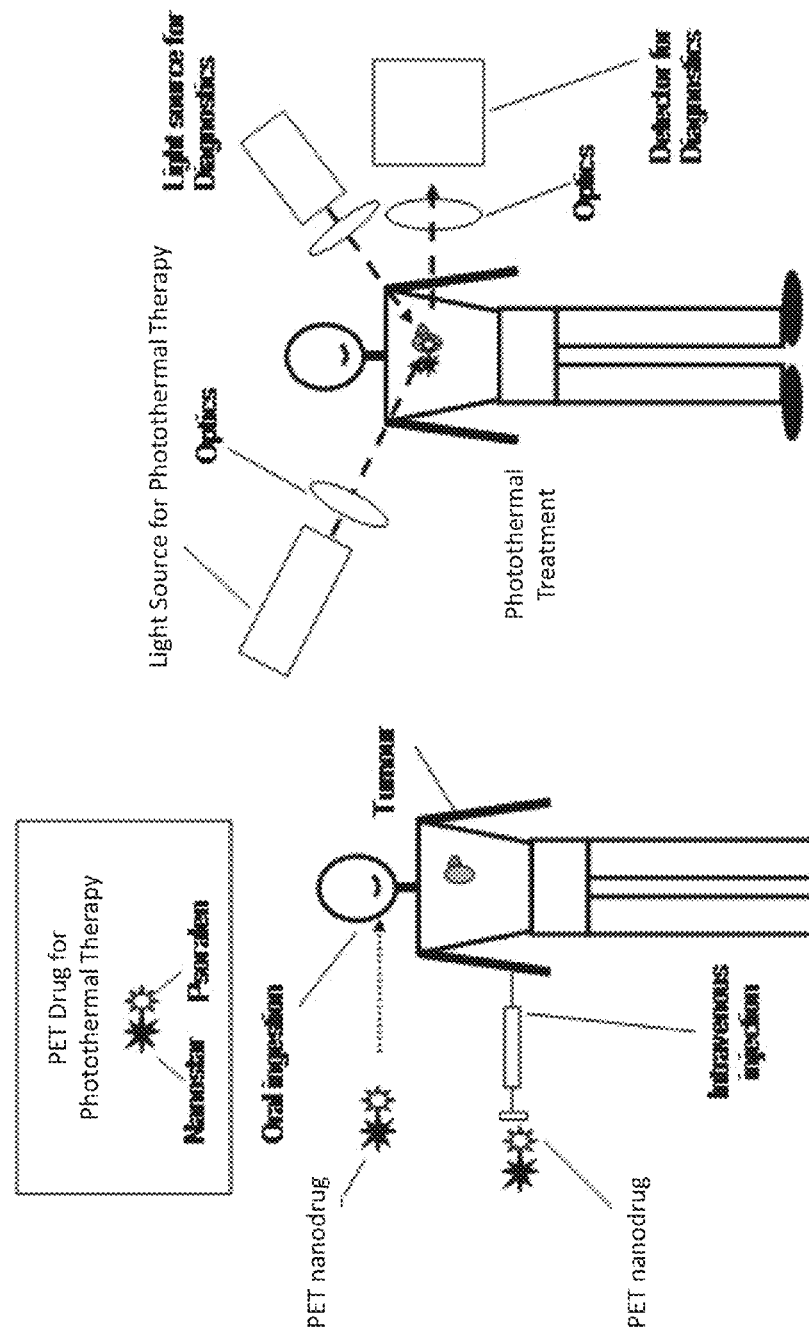
FIGS. 4A-4B are schematic diagrams showing a non-invasive use of a PET- and drug-functionalized nanostar (PET drug) for photothermal therapy and diagnostics according to one or more embodiments of the present disclosure.

Two methods can be used for therapy, single-photon or multi-photon excitation. FIGS. 4A-4B are schematic diagrams showing the non-invasive use of a functionalized nanostar for photothermal therapy according to one or more embodiments of the present disclosure. In one example, nanostars of the present disclosure are functionalized with a positron emission tomography (PET) label and with a drug molecule. The plasmonics-enhanced theranostics (PET) drug molecules are given to a patient by oral ingestion or by intravenous injection. The PET drugs travel through the blood stream inside the body towards the targeted tumor (either via passive or active targeting strategies). If the disease is systematic in nature a photon radiation at a suitable wavelength such as, for example, radio frequency (RF), microwave (MW), infra red (IR), NIR, VIS, UV, and X ray can be used to irradiate the skin of the patient, the light being selected to penetrate deep inside the patient's tissue (e.g., NIR). For solid tumors, the radiation light source can be directed at the tumor. Subsequently, a treatment procedure can be initiated using delivery of energy into the tumor site. One or several light sources may be used as described herein. One example of therapy consists of sending NIR radiation using an NIR laser through focusing optics. The heat can be used to kill diseased cells or tissues. Alternatively, the heat can be used to release psoralen (or another drug of choice).

Figure 5:
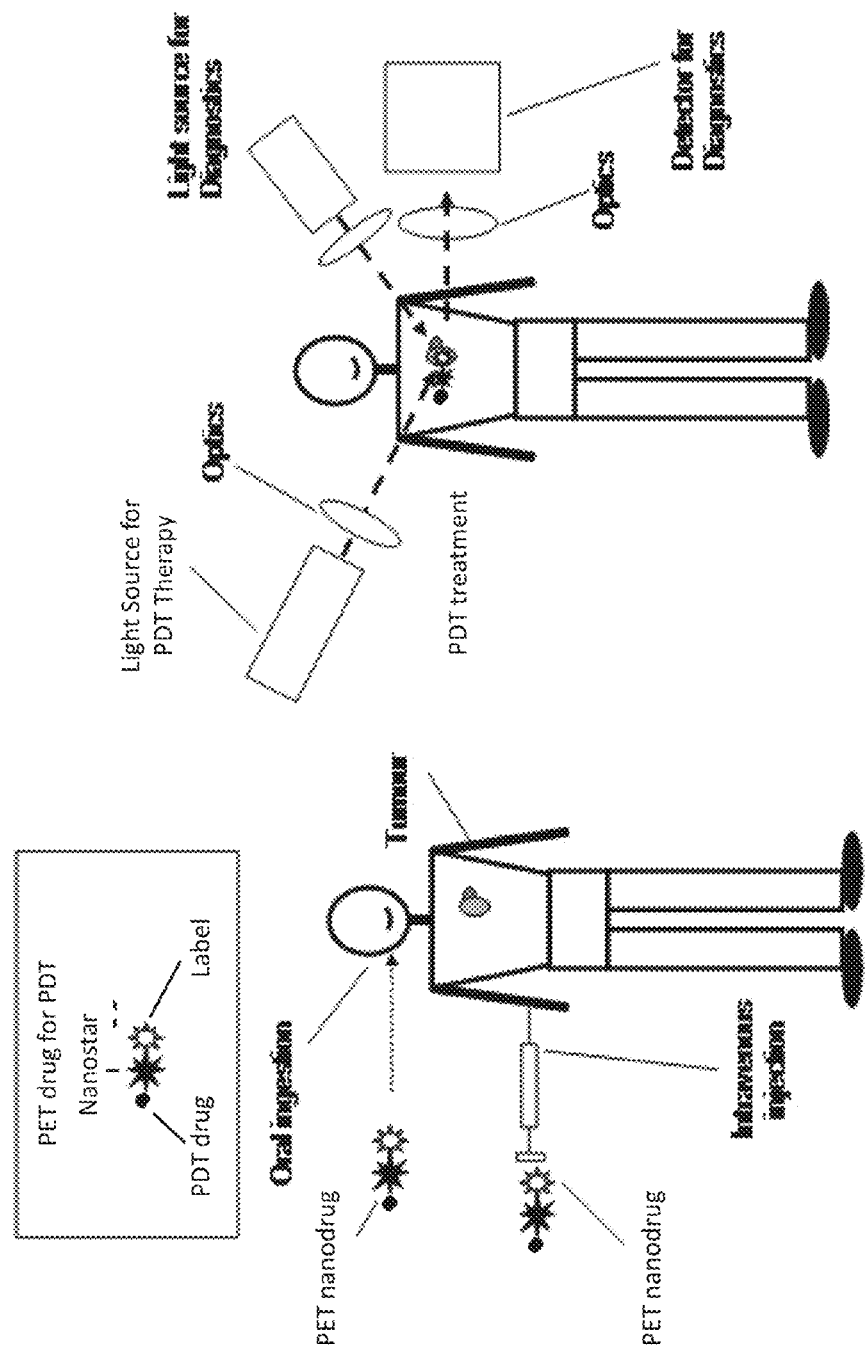
FIGS. 5A-5B are schematic diagrams showing a non-invasive use of a PET- and drug-functionalized nanostar (PET drug) for photodynamic therapy and diagnostics according to one or more embodiments of the present disclosure.

FIGS. 5A-5B are schematic diagrams showing the non-invasive use of a functionalized nanostar for photodynamic therapy (PDT) according to one or more embodiments of the present disclosure. In one example, nanostars of the present disclosure are functionalized with a PET label and with a drug molecule for photodynamic therapy such as, for example, a photosensitizer or a photoactivator molecule. The plasmonics-enhanced theranostics (PET) drug molecules are given to a patient by oral ingestion or by intravenous injection. The PET drugs travel through the blood stream inside the body towards the targeted tumor (either via passive or active targeting strategies). If the disease is systematic in nature a photon radiation at a suitable wavelength such as, for example, radio frequency (RF), microwave (MW), infra red (IR), NIR, VIS, UV, and X ray can be used to irradiate the skin of the patient, the light being selected to penetrate deep inside the patient's tissue (e.g., NIR). For solid tumors, the radiation light source can be directed at the tumor. Subsequently, a treatment procedure can be initiated using delivery of energy into the tumor site. One or several light sources may be used as described herein. One example of therapy consists of sending NIR radiation using an NIR laser through focusing optics. The photodynamic molecule can be used to kill diseased cells or tissues.

Table 1 shows some examples of the plasmonics-active nanostar methods of the present disclosure that combine diagnostics and therapy (Theranostics) using optical and non-optical techniques.

TABLE 1

Examples of Theranostics Methods

| | Treatment Methods | | |
|---|---|---|---|
| | Phototherapy (e.g., Psoralen) | Photothermal therapy | Other optical treatments (e.g., ROS) |
| Detection Methods | | | |
| Fluorescence (1-p, 2-p, multi-p) | x | x | x |
| Phosphorescence | x | x | x |
| Raman | x | x | x |
| Diffuse Scattering | x | x | x |
| Absorption | x | x | x |
| Optical Coherence Methods | x | x | x |
| Photoacoustics | x | x | x |
| X-ray | x | x | x |
| MRI | x | x | x |
| PET | x | x | x |

Focused beam or other radiation including but not limited to such as, for example, X ray, MW, and RF can also be used and will depend upon the treatment methods used. For X-ray excitation, the core of the nanostars can consist of materials that exhibit X-ray excited luminescence (XEOL). There is a wide variety of materials that exhibit XEOL including but not limited to such as, for example, organic, inorganic solids, crystals, lanthanides, polymers.

In one embodiment of the present disclosure, plasmonics-active gold nanostars are provided that result from a process that includes reducing aqueous gold ($Au^{3+}$) to solid gold (Au) in an acidic solution; and mixing a silver salt compound with a weak reducing agent into the solution under conditions such that the plasmonics-active gold nanostars are produced.

In one embodiment, plasmonics-active gold nanostars are provided that result from a process that consists of reducing aqueous gold ($Au^{3+}$) to solid gold (Au) in an acidic solution; and mixing a silver salt compound with a weak reducing agent into the solution under conditions such that the plasmonics-active gold nanostars are produced.

In one embodiment, a method is provided for preparing plasmonics-active gold nanostars free of polymer that includes reducing aqueous gold ($Au^{3+}$) to solid gold (Au) in an acidic solution; and mixing a silver salt compound with a weak reducing agent into the solution under conditions such that the plasmonics-active gold nanostars are produced.

In one embodiment, a method is provided for preparing plasmonics-active gold nanostars free of polymer that consists of reducing aqueous gold ($Au^{3+}$) to solid gold (Au) in an acidic solution; and mixing a silver salt compound with a weak reducing agent into the solution under conditions such that the plasmonics-active gold nanostars are produced.

The $Au^{3+}$ can comprise tetrachloroauric acid ($HAuCl_4$). The $Au^{3+}$ can consist essentially of tetrachloroauric acid ($HAuCl_4$). The $Au^{3+}$ can be reduced to solid Au onto citrate-stabilized gold seeds.

The citrate-stabilized gold seeds used in the method can include or can consist essentially of hollow gold nanoshells and the plasmonics-active gold nanostars that are produced in the method can be hollow. The citrate-stabilized gold seeds used in the method can include or can consist essentially of superparamagnetic particles coated with a layer of gold, and the plasmonics-active gold nanostars that are produced in the method can be superparamagnetic. The superparamagnetic particles used in the method can include or can consist essentially of iron oxide (IO).

The weak reducing agent can consist essentially of ascorbic acid. The silver salt compound can consists essentially of silver nitrate ($AgNO_3$). The concentration of silver cation of the silver compound can range from about 5 µM to about 30 µM and the plasmon peak of the nanostar can range from about 600 nm to about 1000 nm. The ratio of the ascorbic acid to the $HAuCl_4$ can range from about 1.5 to about 2. The nanostars can have a size of less than about 100 nm.

In one embodiment, the plasmonics-active gold nanostars can have one or more of an optical label, a photosensitizer, and a photoactivator. The optical label can include, for example, but is not limited to one or more of a fluorescence label, fluorescein, fluorescein isothiocyanate (FITC), thionine dyes, rhodamine, crystal violet, Raman label, 3,3'-diethylthiatricarbocyanine iodide (DTTC), absorbance label, positively-charged hydrophobic NIR dyes, IR-780, IR-792, IR-797, IR-813, methylene blue hydrate (MB), 4-mercaptobenzoic acid (4-MBA), 5,5'-dithiobis-2-nitrobenzoic acid (DTNB), and 4-aminothiophenol (4ATP).

In one embodiment, the nanostar can include one or both of a layer surrounding the nanostar having within the layer the one or more of the optical label, the photosensitizer, and the photoactivator, and a protective overlayer surrounding the layer.

In one embodiment, a method is provided for treating undesirable cells that includes contacting undesirable cells with the plasmonics-active gold nanostars described above, and applying a single-photon or multi-photon excitation to the undesirable cells such that the undesirable cells are damaged by one or both of thermal energy from the single-photon or multi-photon excitation and thermal energy emitted as a result of excitation of the nanostar by the single-photon or multi-photon excitation.

In one embodiment, in the method the plasmonics-active gold nanostar can further include one or more of a photosensitizer and a photoactivator, wherein the photosensitizer and the photoactivator absorb electromagnetic radiation from one or both of electromagnetic radiation emitted as a result of excitation of the nanostar and directly from the single-photon or multi-photon excitation, such that the undesirable cells are damaged by one or a combination of thermal energy from the single-photon or multi-photon excitation, thermal energy emitted by the nanostar, reactive oxygen species (ROS) generated by the photosensiter, and one or a combination of activation and release of the photoactivator. The photosensitizer can include, for example, but is not limited to a porphyrin, a Protoporphyrin IX, or a methylene blue. The photoactivator can include, for example, but is not limited to a psoralen or a psoralen variant.

In one embodiment of the method, the plasmonics-active nanostar can further include an optical label that absorbs electromagnetic radiation from one or both of electromagnetic radiation emitted as a result of excitation of the nanostar and directly from the single photon or multi-photon excitation such that the optical label emits detectable electromagnetic radiation. The optical label can include, for example, but is not limited to one or more of a fluorescence label, fluorescein, fluorescein isothiocyanate (FITC), thionine dyes, rhodamine, crystal violet, a Raman label, 3,3'-diethylthiatricarbocyanine iodide (DTTC), an absorbance label, a positively-charged hydrophobic near infrared (NIR) dye, IR-780, IR-792, IR-797, IR-813, methylene blue hydrate (MB), 4-mercaptobenzoic acid (4-MBA), 5,5'-dithiobis-2-nitrobenzoic acid (DTNB), and 4-aminothiophenol (4ATP).

In one embodiment, the method can further include detecting the electromagnetic radiation emitted by the optical label by one or more of fluorescence detection, surface enhanced Raman scattering (SERS) detection, surface-enhanced resonance Raman scattering (SERRS), and absorbance detection.

In one embodiment of the method, the nanostar can include one or both of a layer surrounding the nanostar having within the layer the one or more of the optical label, the photosensitizer, and the photoactivator, and a protective overlayer surrounding the layer, such that the optical label, the photosensitizer, and the photoactivator can be released or activated via one or more of passive diffusion release, photochemically triggered release, thermal triggered release, pH triggered release, photochemical activation, and thermal activation.

The undesireable cells can be cells present in a tissue or the undesireable cells can be present in a subject such as, for example, a patient or an animal. In one embodiment of the method, the single-photon or multi-photon excitation can be applied to the tissue or to the subject at an irradiance of about 0.2-0.4 $W/cm^2$ at about 700-900 nm. The undesireable cells can be cancer cells.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

Polymer-Free Synthesis Method for Preparation of High-Yield Monodisperse Gold Nanostars Recently, star-shaped AuNPs ("nanostars") have attracted interest because their plasmon can be tuned to the NIR region, and the structure contains multiple sharp tips that can greatly enhance incident electromagnetic fields. Studies have shown that NIR-absorbing nanorods, nanocages or nanoshells can be used as contrast agents in optical imaging techniques such as optical coherent tomography, two-photon luminescence (TPL) microscopy, and photoacoustic imaging. Their large absorption cross-sections can also effectively convert photon energy to heat during photothermal therapy. Nanostars, which absorb in the NIR, are hypothesized to behave similarly. Nanostar-related bioapplication remain scarce in spite of their potential, mostly due to the difficulty of surface functionalization.

In 2003, Chen et al. [[Chen S, Wang Z L, Ballato, Foulger S H, Carroll D L. *J Am Chem. Soc.* 2003 Dee 31; 125(52):16186-7]] first reported the synthesis of multipod gold nanoparticles from silver plates in the presence of cetyltrimethylammonium bromide (CTAB) and NaOH. Later, several seedless or seed-mediated synthesis methods were employed using majorly poly(N-vinylpyrolidone) (PVP) or CTAB as surfactant. Further use of nanostars has been limited by (1) the potential toxicity of CTAB, (2) the difficulty of replacing PVP or CTAB during biofunctionalization, and (3) induction of aggregation following multiple washes. A polymer-free synthesis can potentially circumvent these issues. In the meantime, previous experimental studies have shown a red-shifting of the plasmon peak from nanostars with longer or sharper branches. Several numerical studies of their plasmonic properties have recently been reported. Hao et al.'s [[Hao F, Nehl C L, Hafner Nordlander P. *Nano Lett.* 2007 March; 7(3):729-32]] 3-D modeling of a single nanostar, consisting of 5 unique branches, with finite difference time domain (FDTD) method showed that nanostars plasmon results from the hybridization of plasmon resonance of each branch; the plasmon peak relative intensity depends on the polarization angle. Senthil et al. [Senthil Kumar P, Pastoriza-Santos I, Rodríguez-González B, Garcia de Abajo F J, Liz-Marzán LM. *Nanotechnology*, 2008:19 (1):015606-12] also stated that the tip angle and radius, but not the number of branches, are the major determining factors in plasmon shift in a simplistic 2-branch model. However, to properly determine the effect of nanostar geometry on the plasmon band, a polarization-averaged multibranched 3-D nanostar model is necessary.

Below is provided a new seed-mediated polymer-free synthesis method that produces high-yield monodisperse gold nanostars with a mean tip-to-tip diameter from 50-70 nm. These nanostars have plasmon bands tunable in the NIR, and use of citrate for stabilization simplifies surface modification for further applications. Their optical properties and plasmonic tunability have been experimentally examined and compared to polarization-averaged 3-D finite element method (FEM) simulation results. Finally, use of nanostars as a strong multiphoton contrast agent during in vitro cellular imaging was investigated.

Anisotropic Growth of Au Branches on Nanostars.

Figure 6:
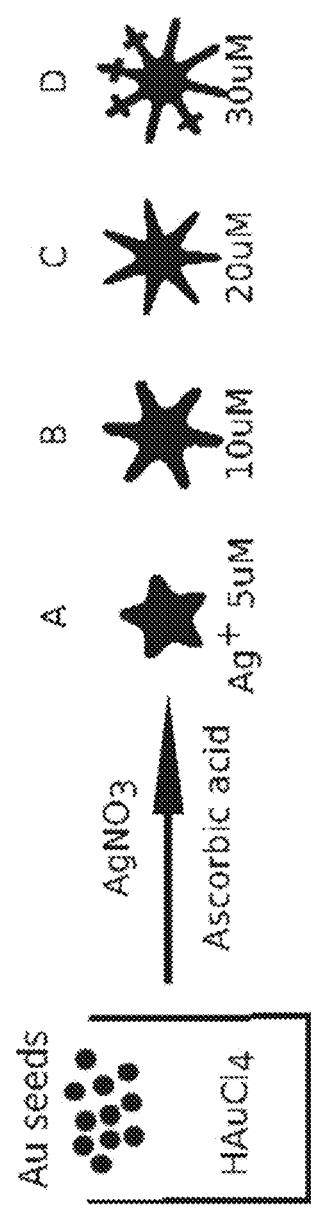
FIG. 6 is a schematic diagram of a synthesis procedure for forming different nanostars according to one or more embodiments of the present disclosure. Increasing silver nitrate concentration is represented as A) 5 μM, B) 10 μM, C) 20 μM, and D) 30 μM.

Nanostars were produced by reducing tetrachloroauric acid onto 12-nm citrate-stabilized gold seeds in an acidic environment using a weak reducing agent, ascorbic acid (AA) (FIG. 6). The synthesis can be rapid, reproducible and does not require a polymer as surfactant. Unlike previous methods which take more than hours of synthesis, the growth of nanostars using this method can be completed in less than half a minute and the particles can be stable at 4° C. for at least a week after centrifugal washing. The method is the simplest and quickest nanostars synthesis to date. The polymer-free synthesis method effectively simplifies surface functionalization of the nanostars.

Figure 7:
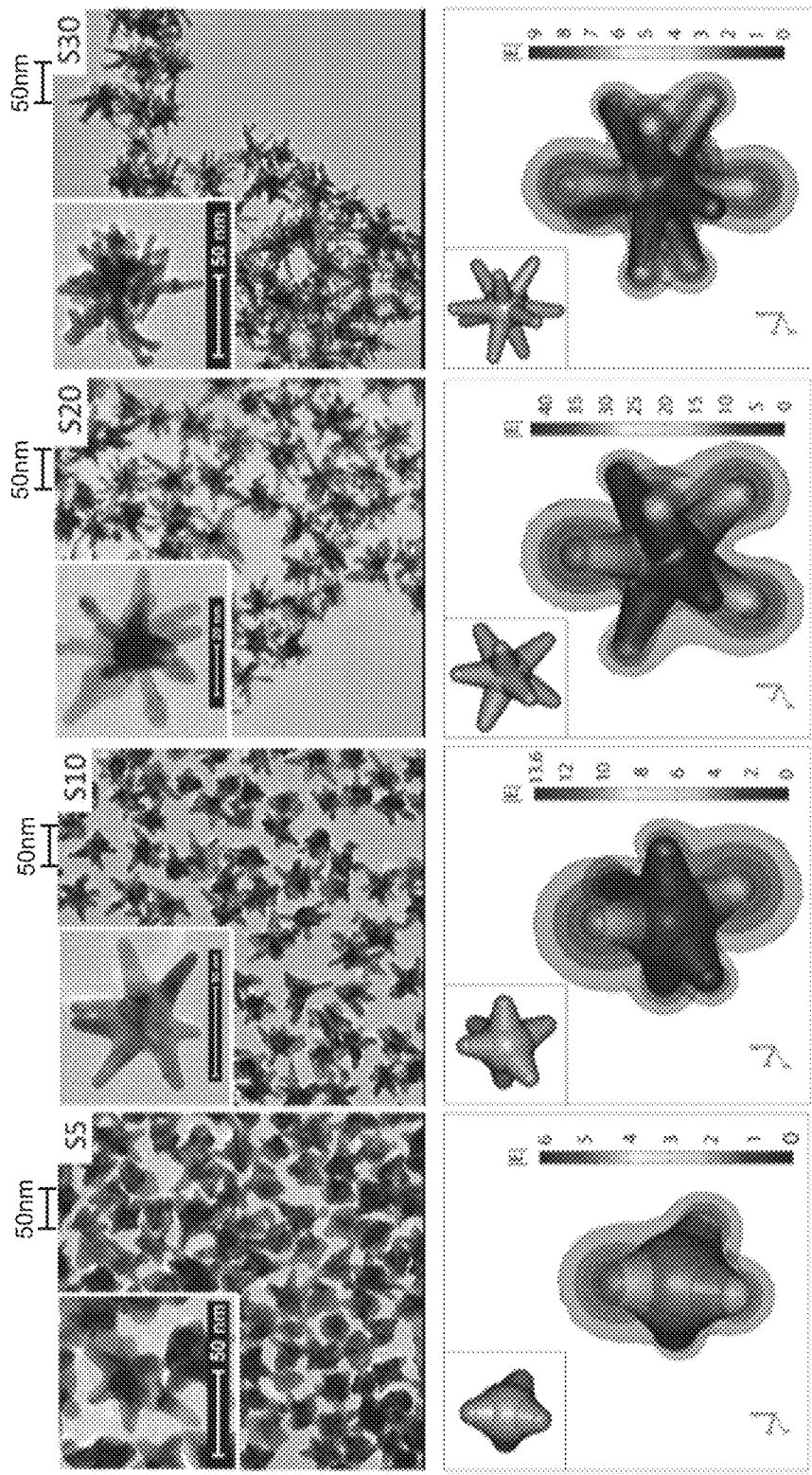
FIG. 7 is a series of TEM images of nanostars formed under different Ag$^+$ concentrations according to one or more embodiments of the present disclosure. The top panel shows increasing Ag$^+$ concentrations as: (S5) 5 μM, (S10) 10 μM, (S20) 20 μM, and (S30) 30 μM. The bottom panel shows simulation of |E| in the vicinity of the nanostars in response to a z-polarized plane wave incident E-field of amplitude 1, propagating in the y-direction and with a wavelength of 800 nm. The insets depict the 3-D geometry of the stars. Diagrams are not to scale.

In order to obtain nanostars of different geometry while keeping the particle size in a similar range, multiple factors were investigated, including pH, vortexing speed, and concentration of $AgNO_3$, AA, $HAuCl_4$ and seed. In general, nanostars formed the most red-shift plasmon under lower pH, higher vortexing speed and $AA/HAuCl_4$ ratio 1.5-2. Concentration of $HAuCl_4$ and seeds was selected so the resulting nanostars sizes were around 60 nm. Importantly, silver ions play a major role in controlling the formation of the star geometry. Without adding $Ag^+$ during synthesis, the resulting particles were polydisperse in both size and shape. The addition of a small amount of $Ag^+$ led to high-yield monodisperse star-shape particles. The overall particles diameters synthesized under different $Ag^+$ concentrations were within 50-70 nm. Under higher $Ag^+$ concentration, sharper and more numerous branches were formed, observable in the TEMs of FIG. 7. Without wishing to be bound to any particular theory of mechanism, the major role of $Ag^+$ is not to form Ag branches but to assist the anisotropic growth of Au branches on multi-twinned citrate seeds, but not single crystalline CTAB seeds, through several possible mechanisms that have been reported for the formation of nanorods, bipyramids and nanostars.

Plasmon Tunability.

Plasmon tunability was achieved by adjusting the $Ag^+$ concentration in the study. Specifically, higher concentrations of $Ag^+$ progressively red-shifted the plasmon band of the nanostars. From TEM images in FIG. 7, higher $Ag^+$ concentrations lead to the formation of longer, sharper, and more numerous branches. Looking at FIG. 7, S5 consists of a few protrusions, while S30 comprises multiple long, sharp branches that appear to branch even further. The overall size is less than 100 nm, which is smaller than previously reported nanostars. FIG. 8 illustrates the nanostars' plasmon peak being tunable from 600 nm to 1000 nm by adjusting the $Ag^+$ concentration. This was accompanied by a visible change in the solution color from dark blue to dark grey as the plasmon red-shifts and broadens. Both the plasmon peak position and spectral width (as defined by the full width at half maximum (FWHM) of the plasmon peak) followed a linear trend with increasing $Ag^+$ concentration. A plateau was reached around a $Ag^+$ concentration of 30 μM in this study. Nanostars can therefore be synthesized in a controlled fashion and applied in NIR applications.

Numerical Simulations.

A simulation that models and compares the optical properties of different nanostars was performed. Instead of modeling the plasmon of a single polarization, this analysis featured polarization-averaging over space as the nanostars were discretely rotated at 6 angles, a feature that has not been addressed so far. The 3-D nanostar simulations were performed using the finite element method (FEM), which yields solutions to the local field around 3-D metallic nanostructures that are in excellent agreement with theory. For each of the 4 nanostars, the local E-field is most greatly enhanced at the tips of those branches that are at least partially aligned parallel to the incident polarization, most clearly observable for the top-most branch that is aligned parallel to the polarization (data not shown). Notably, the E-field at the surface of all branches is enhanced to a value of at least between 1 and 4, suggesting that these surfaces also contribute to the total E-field enhancement around the nanostar.

It was demonstrated here that the experimental absorption peak shifts that were observed can be modeled by designing a 3-D nanostar geometry according to the parameters including core diameter, branch base width, branch length and tip radius. The modeled absorption peaks of the various nanostars align well with the experimentally-measured spectra, and reproduce experimentally observed peaks for each nanostars solution sample (data not shown). A weak absorption around 520 nm was attributed to the plasmon resonance of the nanostar's core, and a dominant plasmon band at longer wavelengths was observed due to the resonance supported by the nanostar branches. As the number of branches increases from 4 to 10, the peak absorption cross-section increase from S5 to S30 (see FIG. 7 top), respectively. Moreover, the deviation from the average intensity from average decreases with increasing branch number (see FIG. 7 top).

Materials.

Gold(III) chloride trihydrate ($HAuCl_4$), sodium citrate tribasic dihydrate, L(+)ascorbic acid (AA), 4-mercaptobenzoic acid (pMBA), silver nitrate ($AgNO_3$), hydrochloric acid (HCl), methanol (MeOH), 0-(3-Carboxypropyl)-O'-[2-(3-mercaptopropionylamino)-ethyl]-polyethylene glycol (Mw 5000; PEG5000), *Triticum vulgaris* lectin (wheat-germ agglutinin; WGA) and rhodamine B were purchased from Sigma-Aldrich (St. Louis, Mo.). DAP1, FM 1-43, RPMI 1640, insulin, fetal bovine serum were purchased from Invitrogen (Carlsbad, Calif.). 16% paraformaldehyde was purchased from Alfa Aesar (Ward Hill, Mass.). (Orthopyridyl)disulfide PEG2ooo-Succinimidyl Ester) (Mw 2000; OPSS-PEG2ooo-NHS) was purchased from Creative PEG-Works (Winston Salem, N.C.). All chemicals were used as received. Millipore Synergy ultrapure water (resistivity=18.2 MΩ cm) was used in all aqueous solutions. All glassware and stir bars were cleaned with aqua regia solution and oven-dried before use.

Synthesis of Au Seeds.

A modified Turkevich method was used to prepare a seed solution. Briefly, 10 ml of a 38.8 mM citrate solution was added into 100 ml of a boiling 1 mM $HAuCl_4$ solution under vigorous stirring while keeping the volume remained roughly unchanged. After boiling for about 30 min, the solution was cooled, filtered by a 0.22 micron nitrocellulose membrane, and kept at 4° C. for long-term storage.

Synthesis of Au Nanostars.

Nanostars were prepared by a seed-mediated growth method. Briefly, 100 µl of the above seed solution (12±0.7 nm; $A_{520}$: 2.81) was added to 10 ml of 0.25 mM $HAuCl_4$ solution (with 10 µl of 1N HCl) in a 20 ml glass vial at room temperature under vigorous stirring. Quickly, 100 µl $AgNO_3$ at different concentrations (5 to 30 µM) and 50 µl of AA (100 mM) were added simultaneously. The solution was stirred for 30 sec as its color rapidly turned from light red to blue or greenish-black. Immediately afterwards, two centrifugal washes at 3000-5000 rcf were performed in 15 ml tube to halt the nucleation. The solution was redispersed in 2 mM pH7 citrate buffer, filtered by a 0.22 µm nitrocellulose membrane, and then kept at 4° C. for long-term storage.

Instrumentation.

The structural features of the nanostars were characterized using transmission electronic microscopy (TEM; Fei Tecnai $G^2$ Twin, 200 kV) and analyzed using ImageJ software (National Institute of Health). The particle hydrodynamic size distribution and concentration were determined by nanoparticle tracking analysis (NTA 2.1; build 0342) using NanoSight NS500 (Nanosight Ltd. UK). Absorbance spectra were obtained using a dual-beam spectrophotometer (Shimadzu UV-3600; Shimadzu corporation, Japan) or a microplate reader (BMG LABTECH FLUOStar Omega; BMG LABTECH GmBH, Germany). More than five samples were analyzed for each synthesis condition. Morphological features were assessed from more than 50 particles on different TEM images. Data values were represented by mean±1 standard deviation.

Modeling.

The 3-D nanostar simulations were performed using the finite element (FEM) based Comsol Multiphysics v3.4 software package and the RF module (Comsol, Inc. Burlington Mass., USA). A unique, 3-D nanostar model was designed for each of the samples S5, S10, S20 and S30 using the dimensions obtained from their corresponding TEM images (data not shown). For a particular star model, the branches protrude normal to the core surface, but were randomly positioned on the core such as to maximize the inter-branch distance.

The dielectric function of gold was modeled using the Lorentz-Drude model for gold from Johnston and Christy's and the surrounding medium was modeled as water with a refractive index n=1.33. The computational domain was bounded by a spherical perfectly matched layer (PML) to prevent any reflections back onto the nanoparticle. The nanostars were excited with a z-polarized incident plane wave of E-field amplitude 1, propagating along the y-axis and of wavelength ranging 300 nm to 1200 nm. The nanoparticles were meshed such that the largest mesh size on the star's surface was limited to 3 nm, ensuring high meshing density and thus good spatial sampling. The orientation dependence of the incident E-field was accounted for by averaging the absorption spectra of the nanostars as they were incrementally rotated by 30 degrees in the [x=y] plane, such that the orientation of the branches relative to the z-polarized incident field became randomized.

Example 2

Preparation of Hollow Gold Nanostars

Figure 9:
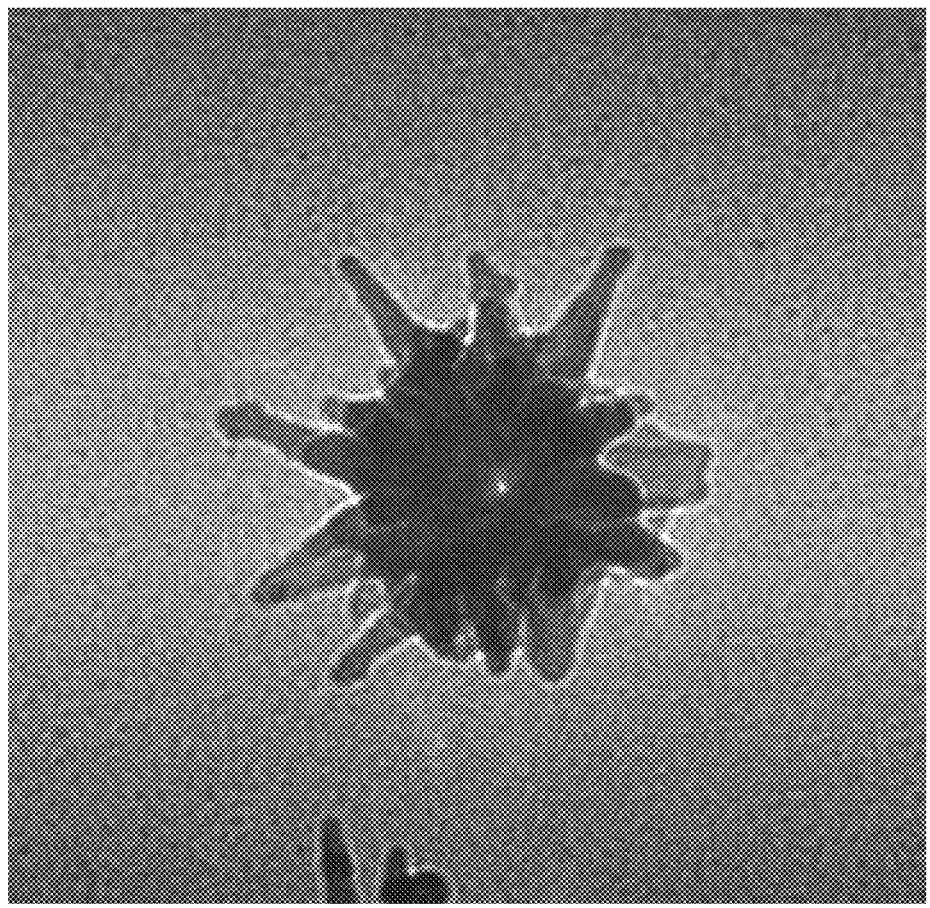
FIG. 9 is a TEM micrograph of hollow gold nanostar according to one or more embodiments of the present disclosure.

Hollow gold nanostars were prepared using the same seed-mediated growth method described above in Example 1 and are shown in FIG. 9. Use of hollow gold nanoshells as the seed particle in the method of Example 1 allows for the growth of branches while keeping the hollow interior intact. Such particles have similar applications to regular gold nanostars, with the added advantage of drug or other small molecule encapsulation within the hollow interior.

Example 3

Preparation of Magnetic Core Gold Nanostars

Figure 10:
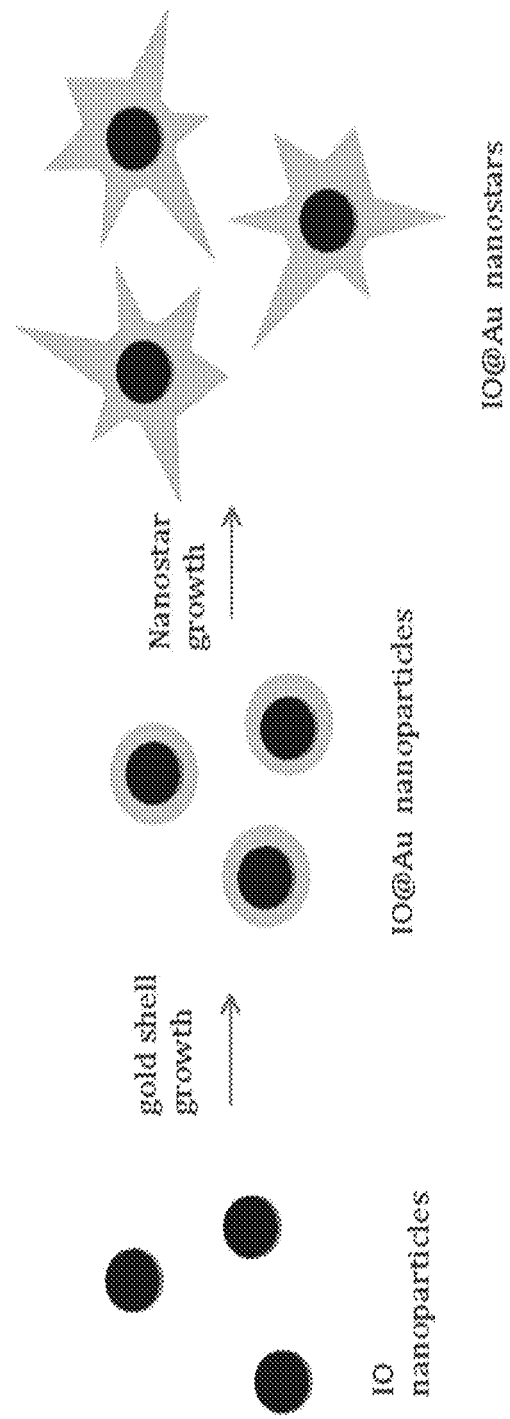
FIG. 10 is a schematic diagram of a process for synthesizing a magnetic gold nanostar according to one or more embodiments of the present disclosure.

Gold nanostars that have superparamagnetic cores can be synthesized by first coating superparamagnetic iron oxide (IO) particles with a layer of gold (IO@Au), then using these IO@Au particles as seeds in the gold-nanostar synthesis procedure described above in Example 1. Such particles have similar applications to regular gold nanostars, with the added advantage that the magnetic core nanostars can be manipulated by an external magnetic field. A schematic of this process is shown in FIG. 10.

Example 4

Imaging of Nanostars Using Two-Photon Photoluminescence (TPL)

Recently, efficient plasmon-enhanced two-photon photoluminescence (TPL) gold nanoparticles (e.g. nanorods, nanoshells, nanocages) have been used as a contrast agent in several reports. On metal nanoparticles, the resonant coupling of the plasmon band with the incident laser greatly amplifies the nanoparticles TPL, typically increasing the two-photon action cross sections (TPACS) of NIR-absorbing nanoparticles above those of organic fluorophores. TPL can therefore be applied to multiphoton microscopy, offering a convenient way to visualize NIR-absorbing gold nanoparticles in tissue using NIR lasers.

Gold nanostars, with plasmons in the NIR, show greatly enhanced TPL. A quadratic dependence of TPL intensity on excitation power suggests the existence of an underlying non-linear two-photon process on nanostars (data not shown). Such dependence was not seen on 60 nm gold or silver spheres solution (data not shown). The TPL excitation spectra of S20 and S30 match their plasmon spectra (see FIG. 7), indicating that nanostars (like nanorods) enhance TPL via plasmon coupling. Similar to previous reports, the excitation spectra are narrower than the plasmon spectra, probably due to the non-linear properties of TPL. Interestingly, the concentration normalized emission intensity at 800 nm of nanostars solutions were found to be $1.1 \times 10^4$ greater than that of Rhodamine B, making the TPACS of nanostars more than a million GM (data not shown). Meanwhile, the emission intensities from each nanostars solutions were found to be similar on the 3 different detection channels on the microscope. The broad emission spectrum implies that TPL from nanostars, like nanorods, may be a result of electron-hole recombination or thermal radiation, without wishing to be bound to any particular theory of mechanism. Because a typical NIR dye possesses minimal TPACS, the reason for such high TPACS from NIR-absorbing nanostars remained to be clarified.

Polymer-free nanostars with such a high TPACS can be used as a strong contrast agent in TPL imaging in biological samples. Here, we demonstrate TPL imaging of WheatGerm Agglutinin (WGA) functionalized nanostars on BT549 cancer cells. A preferential binding of WGA-coated nanostars on the cell membrane was observed (data not shown). In contrast, PEG-coated nanostars bound poorly. Numerous white spots representing nanostars covered the cell membrane. The white color was a composite result of the similar intensity on 3 different detection channels, indicating a broad TPL emission spectrum from nanostars. The nanostars emitted strongly without photobleaching under low laser power (4 mW), which is in the typical working range for organic fluorophores. No signal was observed from WGA-coated spheres under the same experimental settings (data not shown). Interestingly, photobleaching of nanostars was observed after several scans at higher power (>10 mW), possibly due to a structural damage of the plasmon-generating an isotropic features. TPL imaging therefore substantiates the biological use of these polymer-free nanostars. Exploiting its strong TPACS, nanostars imaging and tracing without the need for fluorophores is possible.

In conclusion, synthe plasmonically tunable gold nanostars were synthesized which allowed for simple surface functionalization. The synthesis was quick and polymer-free. As branch AR increases from nanostars S5 to S30, the plasmon peaks are shifted to the NIR region. Sharp branches interact more intensely with NIR laser excitation, and play a key role in determining the optical properties of the nanostars. Three dimensional models of the nanostars were numerically solved to deduce a good agreement between experimental and theoretical absorption spectra, with the number of branches contributing to peak intensity and branch AR to plasmon shift. Exploiting the high TPACS, biomolecule-functionalized nanostars can be used as a strong contrast agent for multiphoton microscopy as well as other NIR imaging techniques.

Materials.

Gold(III) chloride trihydrate (HAuCl4), sodium citrate tribasic dihydrate, L(+)ascorbic acid (AA), 4-mercaptobenzoic acid (pMBA), silver nitrate ($AgNO_3$), hydrochloric acid (HCl), methanol (MeOH), O-(3-Carboxypropyl)-O'-[2-(3-mercaptopropionylamino)-ethyl]polyethylene glycol (Mw 5000; PEG5000), Triticum vulgaris lectin (wheat-germ agglutinin; WGA) and rhodamine B were purchased from Sigma-Aldrich (St. Louis, Mo.). DAP1, FM 1-43, RPMI 1640, insulin, fetal bovine serum were purchased hom Invitrogen (Carlsbad, Calif.). 16% paraformaldehyde was purchased from Alfa Aesar (Ward Hill, Mass.). (Orthopyridyl)dis ul:fidePEG2ooo-Succinimidyl Ester) (Mw 2000; OPSS-PEG2ooo-NHS) was purchased from Creative PEG-Works (Winston Salem, N.C.). All chemicals were used as received. Millipore Synergy ultrapure water (resistivity=18.2 MO em) was used in all aqueous solutions. All glassware and stir bars were cleaned with aqua regia solution and oven-dried before use.

Synthesis of Au Seeds.

A modified Turkevich method was used to prepare a seed solution. Briefly, 10 ml of a 38.8 mM citrate solution was added into 100 ml of a boiling 1 mM $HAuCl_4$ solution under vigorous stirring while keeping the volume roughly unchanged. After boiling for about 30 min, the solution was cooled, filtered by a 0.22 micron nitrocellulose membrane, and kept at 4° C. for long-term storage.

Synthesis of Au Nanostars.

Nanostars were prepared by a seed-mediated growth method. Briefly, 100 µl of the above seed solution (12±0.7 nm; $A_{520}$: 2.81) was added to 10 ml of 0.25 mM $HAuCl_4$ solution (with 10 µl of 1N HCl) in a 20 ml glass vial at room temperature under vigorous stirring. Quickly, 100 µl $AgNO_3$ at different concentrations (5 to 30 µM) and 50 µl of AA (100 mM) were added simultaneously. The solution was stirred for 30 sec as its color rapidly turned from light red to blue or greenish-black. Immediately afterwards, two centrifugal washes at 3000-5000 rcf were performed in 15 ml tube to halt the nucleation. The solution was redispersed in 2 mM pH7 citrate buffer, filtered by a 0.22 µm nitrocellulose membrane, and then kept at 4° C. for long-term storage.

Instrumentation.

The structural features of the nanostars were characterized using transmission electronic microscopy (TEM; Fei Tecnai $G^2$ Twin, 200 kV) and analyzed using ImageJ software (National Institute of Health). The particle hydrodynamic size distribution and concentration were determined by nanoparticle tracking analysis (NTA 2.1; build 0342) using NanoSight NS500 (Nanosight Ltd. UK). Absorbance spectra were obtained using a dual-beam spectrophotometer (Shimadzu UV-3600; Shimadzu corporation, Japan) or a microplate reader (BMG LABTECH FLUOStar Omega; BMG LABTECH GmBH, Germany). More than five samples were analyzed for each synthesis condition. Morphological features were assessed from more than 50 particles on different TEM images. Data values were represented by mean±1 standard deviation.

Modeling.

The 3-D nanostar simulations were performed using the finite element (FEM) based Comsol Multiphysics v3.4 software package and the RF module (Comsol, Inc. Burlington Mass., USA). A unique, 3-D nanostar model was designed for each of the samples S5, S10, S20 and S30 using the dimensions obtained from their corresponding TEM images (data not shown). For a particular star model, the branches protrude normal to the core surface, but were randomly positioned on the core such as to maximize the inter-branch distance.

The dielectric function of gold was modeled using the Lorentz-Drude model for gold from Johnston and Christy's and the surrounding medium was modeled as water with a refractive index n=1.33. The computational domain was bounded by a spherical perfectly matched layer (PML) to prevent any reflections back onto the nanoparticle. The nanostars were excited with a z-polarized incident plane wave of E-field amplitude 1, propagating along the y-axis and of wavelength ranging 300 nm to 1200 nm. The nanoparticles were meshed such that the largest mesh size on the star's surface was limited to 3 nm, ensuring high meshing density and thus good spatial sampling. The orientation dependence of the incident E-field was accounted for by averaging the absorption spectra of the nanostars as they were incrementally rotated by 30 degrees in the [x=y] plane, such that the orientation of the branches relative to the z-polarized incident field became randomized.

Two-Photon Microscopy Instrumentation.

The two-photon photosluminescence (TPL) images were recorded using a commercial multiphoton microscope (Olympus FV1000, Olympus America, Center Valley, Pa.)

with 3 detection channels (420-460 nm, 495-540 mn, 575-630 nm) on photomultiplier tubes (H7422-40, Hamamatsu, Bridgewater, N.J.). A femtosecond Ti:Sapphire laser (Chameleon Vision II, Coherent, Santa Clara, Calif.) with tunable range 680-1080 nm, 140 fsec pulse width and 80 MHz repetition rate was used. The laser beam was focused through a 25× 1.05NA water-immersion objective (XLPL25XWMP, Olympus America, Center Valley, Pa.). Time-correlated single photon counting fluorescence lifetime was measured on the same microscope system using PicoHarp 300 counting electronics (PicoQuant GmBH, Berlin, Germany).

Two-Photon Action Cross Section (TPACS) Measurement of Nanostars.

The TPACS of gold nanostars (0.1 nM in 2 mM citrate buffer) were measured by comparing the two-photon photoluminescence of nanostars with fluorescence of Rhodamine B (100 nM in pure MeOH) at 800 nm excitation. The TPACS has a unit of $cm^4s$, where 1 Goeppert-Mayer unit (GM) represents $10^{-50}$ $cm^4s$/photon. The excitation power was 2 mW.

Luminescence/fluorescence intensity was integrated over an image area of 250×250 $\mu m^2$ under 10 $\mu s$/pixel and 256×256 resolution. The sample solution was placed on a depression slide covered by a coverslip during imaging.

Cell Culture;

The BT549 cancer cells were a gift from Victoria Seewaldt's lab. Cells were incubated in RPMI 1640 culturing media, containing 10% of fetal bovine serum and 0.023 U/ml of insulin, in an incubator with a humidified atmosphere (5% $CO_2$). Cells in exponential growth phase were used in experiments.

TPL Cellular Imaging.

Nanostars were conjugated with WGA using a heterobifunctional crosslinker OPSS-PEG$_{2000}$-NHS based on a previous protocol. WGA has high affinity to glycoproteins and glycolipids on the cell membrane therefore WGA-conjugated nanostars can be seen on cell surface. Nanostars conjugated with PEG$_{5000}$ were used as control. Functionalized nanostars were washed and resuspend to a final concentration 0.1 nM in PBS. Paraformaldehyde (4%, 10 min) fixed cells, pretreated with FBS blocking for 3 min and PBS washes, underwent 10 min incubation with WGA-nanostars or PEG-nanostars followed by PBS washes. Counterstain with Hoescht 33342 and FM 1-43 FX were performed according to the company's protocols. Two-photon imaging was done under 1% transmission, 10 $\mu s$/pixel and 512×512 resolution with 4-frame Kalman averaging. All 3 channels were set to 550 gain (for WGA-nanostar)/600 gain (for PEG-nanostar) and 8 offset.

Example 5

Photothermal Properties of Nanostars

Selective localized cancer treatment can be achieved when the laser irradiates a tumor concentrated with nanostars that can act as an efficient photothermal transducer. The plasmonic gold nanostars of the present disclosure offer such a unique capability to transduce photon energy to heat when excited in the near infrared (NIR) tissue therapeutic window. The gold nanostars, with their small core size and multiple long thin branches, exhibit high absorption cross sections that are tunable in the NIR region with relative low scattering effect, rendering them efficient photothermal transducers. Here, photothermal ablation was demonstrated in SKBR3 breast cancer cells incubated with nanostars synthesized according to the method described in Example 1 undergoing laser irradiation of different durations. Also, a regional hyperthermia to 45° C. was observed when irradiating a region injected with the nanostars. The results of plasmon-enhanced localized hyperthermia have illustrated the usefulness of gold nanostar as an efficient photothermal agent in cancer therapy.

Materials.

Gold(III) chloride trihydrate (HAuCl4), sodium citrate tribasic dehydrate (Na$_3$Cit), L(+)-ascorbic acid (AA), silver nitrate (AgNO3), 0-(3-Carboxypropyl)-0'-[2-(3-mercaptopropionylamino)ethyl)-polyethylene glycol (Mw 5000; SHPEG5ooo), were purchased from Sigma-Aldrich (St. Louis, Mo.). McCoy 5A, fetal bovine serum, Hoescht 33342, FM 1-43FX were purchased from Invitrogen (Carlsbad, Calif.). All chemicals were used as received. Millipore Synergy ultrapure water (resistivity=18.2 MQ cm) was used in all aqueous solutions. All glassware and stir bars were cleaned with aqua regia solution and oven-dried before use.

Gold Nanostars Synthesis.

Gold nanostars were synthesized as described in Example 1 herein above.

Gold Nanostars Characterization.

Transmission electronic microscopy (TEM; Fei Tecnai G2 Twin, 200 kV) was used for structural analysis. The particle hydrodynamic size distribution, concentration, and s-potential were determined by nanoparticle tracking analysis (NTA 2.1; build 0342) using NanoSight JSSOO (Nanosight Ltd. UK). A UV-VIS spectrophotometer (Shimadzu UV-3600; Shimadzu corporation, Japan) was used to collect the extinction spectrum.

Cell Culture and Incubation with Gold Nanostars.

The SKBR3 breast cancer cells were cultured in McCoy 5A culturing media (10% fetal bovine serum) in an incubator with a humidified atmosphere (5% CO2) according to the ATCC's protocol. Cells in exponential growth phase were used in experiments. The cells were seeded into 35 mm petri dishes for more than 2 days until ~80-90% confluency. Unlabeled nanostars (0.3 nM particle concentration) were suspended and sonicated in the same growth media immediately before use. Nanostars functionalized with SHPEG5ooo 5 $\mu M$ were washed and resuspended (0.3 nM) in growth media. Then, cells were incubated 1 hour with 1 ml of (1) unmodified nanostars in media, (2) PEGylated nanostars in media and (3) media alone. Before the PTT, cells were washed by PBS twice and replaced with new media. Another set of cells were fixed by 4% paraformaldehyde and imaged under multiphoton microscopy (Olympus FV 1000, Olympus America, Center Valley, Pa.) to confirm the presence of nanostars in cells. Cells were stained with Hoescht 33342 (2 $\mu g$/ml in PBS) and FM 1-43 FX (4 $\mu g$/ml in PBS) 30 min prior to imaging.

Phorothermal Therapy and Viability Staining.

On a 37° C. heating stage, cells with 90% confluency were exposed to 980 nm diode laser irradiation (15 W/cm$^2$, spot size 8 mm$^2$) for 1, 3, and 5 min. Both nanostar-treated and untreated samples receiving no laser irradiation were used as control. After 1 day, cells were examined by a live-cell staining using Fluorescein diacetate (FDA; 1 $\mu g$/ml in PBS, incubated for 30 min) under a fluorescence microscope. Non-fluorescent FDA is converted to green fluorescent fluorescein by esterase in living cells.

In Vivo Photothermal Treatment.

A nude athymic mouse was anesthetized by ketamine and kept warm on a 37° C. heating stage. A 50 $\mu l$ of PEGylated gold nanostars solution (6 nM in PBS) was injected subcutaneously on one side of thigh with saline injection on the other thigh as control. The injection sites were irradiated (980 nm, 0.56 W/cm2, spot size 1 cm2) for 5 min. The temperature was measured by a needle thermocoupler before and after the laser irradiation. The animal experiments were conducted in compliance with the guidelines for the care and use of research animals by IACUC.

In this study, plasmon tunable gold nanostars were employed as a new photothermal transducer for hyperthermic therapy. Based on theoretical calculations, at the plasmon peak, nanostars achieve an absorption to scattering cross section ratio greater than the nanorods and nanoshells. In vitro, nanostars locate predonantely in the cytoplasm, as investigated by the two-photon photoluminescence imaging. The photothermal response was maximal when both NIR laser excitation and nanostars incubation were combined but only minimal when separated. The localized cell death intensified after longer irradiation suggesting a laser dose dependency.

Nanostars were synthesized with size around 60-70 nm. The synthesis was simple without the use of polymer. TEM showed star-shaped particles with 8-10 protruding branches on a small core. Some branches even had additional small branches on them. Nanostars exhibit a broad plasmon spectrum, which peaks at 890 nm with a molar absorptivity of $6.7 \times 10^9$ M-1 cm-1 The hydrodynamic size was 70±32 nm and the ζ-potential was −31.3 mV by nanoparticle tracking analysis. Upon addition of the serum-containing culturing media, the plasmon peak redshifted, suggesting possible aggregation.

The nanostars efficiently absorb NIR energy. The modeled nanostar had plasmon peaks at 960 nm with the absorption to scattering ratio of nanostar 9.2. The theoretical simulation results indicate that nanostars predominately absorb rather than scatter the incident photoenergy in the simulation. It was determined that the branches aspect ratio, but not the core size or branch number, contributes the major role for the red-shifted plasmon. Here, the modeled nanostars have the aspect ratio changed from 1.46 to 2.1 with branch number increased from 8 to 10 and core size decreased from 23.7 to 21.7. At their plasmon peaks, the absorption to scattering ratios ($C_{Abs}/C_{Sca}$) of nanostar A and B are 10.7 and 9.2, respectively (Table 2).

TABLE 2

Calculated cross section comparison of aspherical gold nanoparticles (AuNPs)

| | $C_{Abs}$ ($10^{-15}$ m$^{-2}$) | $C_{Sca}$ ($10^{-15}$ m$^{-2}$) | $C_{Abs}/C_{Sca}$ |
|---|---|---|---|
| Nanorods, width: 17.9, R: 3.9, at 820 nm | 16.9 | 5.0 | 3.38 |
| Nanoshells, R1/R2: 60/70 nm, at 892 nm | 50.9 | 32.5 | 1.57 |
| Nanocages, core: 30 nm, at 825 nm | 7.3 | 0.8 | 9.1 |
| Nanostars A, at 810 nm | 11.4 | 1.07 | 10.7 |
| Nanostars B, at 960 nm | 14.0 | 1.52 | 9.2 |

Compared to other classes of aspherical AuNPs, nanostars have comparable ratio to nanocages, but much higher ratio than norods and nanoshells. Because the scattering is proportional to the particle size, the nanocages of 30-nm core typically have smaller scattering cross section. For nanostars, although the tip-to-tip diameter is 70-nm, the core size is small and branches are thin. The scattering thus is smaller than 70-nm of nanorods and nanoshell. Since it is desirable to have low scattering and high absorption, nanostars can be a better candidate agent for photothermal therapy. Furthermore, nanostars efficiently absorb NIR energy in the therapeutic window region. In a solution filled with 1 nM and 0.1 nM nanostars excited by 980 nm CW laser of 1.2 W, the temperature rose to 80° C. and 60° C. respectively in 5 min (data not shown). Meanwhile, the 2-mM citrate solution only rose to 40° C. under the same laser excitation. To avoid thermal damage from the 980-nm laser itself, the possible laser excitation time was set to less than 5 min.

Prior to PTT experiments, the uptake of nanostars was investigated by two-photon luminescence (TPL) microscopy. Because nanostars possess a high two-photon action cross section, the presence of nanostars in cells can be easily detected under a commercial multi-photon microscopy. After one-hour of incubation, bright nanostars signal could be seen only in cells receiving media-treated nanostars (data not shown). Even without any surface functionalization, the nanostars located predominately in the cytoplasm but not the nucleus displaying a ring pattern on the image. Cells receiving no nanostars showed only weak autofluorescence (data not shown).

In one experiment, separated wells filled with 3 nM and 0.3 nM PEGylated nanostars 200 μl were irradiated by 980 nm CW diode laser (15 W/cm$^2$, 0.08 cm$^2$); the temperature rose to 80° C. and 60° C. respectively in 5 min (data not shown). The nanostar-free Na$_3$Cit buffer rose to 40° C. under the same laser irradiation, suggesting a relatively low but potential risk of thermal damage under this power density. To avoid thermal damage from the 980 nm laser itself, the laser irradiation time was set to maximal of 5 minutes. Prior to PTT experiments, the uptake of nanostars was investigated by two-photon luminescence (TPL) microscopy. After one-hour of incubation, bright dots representing nanostars could be seen only in cells incubated with nanostars but not PEGylated nanostars (data not shown). These unlabeled nanostars located predominately in the cytoplasm displaying a ring pattern on the image. Meanwhile, cells incubated with no nanostars showed only dye signals (data not shown). The photothermal response on SKBR3 cells was measured using 3 different laser treatment durations (data not shown). With the presence of nanostars, cancer cells were killed after 3 or 5 min but were not visibly harmed after 1 min of laser irradiation. Once dead, cells in the treated region detached before imaging. The photothermal response was higher at 5 min than at 3 min reflecting the laser dose dependency. Cells without nanostars were viable until 5 minutes of irradiation, when a small region of cells began to die. This was probably due to the temperature elevation from the laser irradiation itself, although the ablated area was much smaller than cells treated with nanostars and laser combined. Meanwhile, cells incubated with nanostars but not treated with the laser maintained their viability. Thus, no apparent cytotoxicity was observed from nanostars during the study period.

The photothermal response in vivo was examined by irradiating a region injected subcutaneously with PEGylated nanostars (data not shown). A bluish bulging discoloration was the area of nanostars injection. Saline injection resulted in quick dispersion with no visible elevation. The laser spot size was adjusted to 1 cm$^2$ to cover the injection site. In 5 min, the temperature rose from 32.8 to 45° C. For saline control, the temperature increased to 39.5° C.

The effectiveness of nanostars as photothermal transducers has been demonstrated by the study described herein. First, the synthesis of NIR absorbing nanostars can be performed in only minutes, which is much quicker than other classes of aspherical AuNPs that can take more than hours to synthesize. Second, since it is desirable to have low scattering and high absorption, nanostars can be a better agent for photothermal therapy. From the simulation results, nanostars were shown to have compatable Abs/Sca ratio to nanocages, but much higher ratio than nanorods and nanoshells. Because the scattering is proportional to the particle size, the nanocages of 30-nm core typically have smaller scattering cross section. For nanostars, although the tip-to-lip diameter is 70-nm, the core size is small and branches are thin. Thus, the scattering for nanostars of 70-nm is smaller than that of nanorods and nanoshells of 70-nm.

The photothermal response is determined by the both nanostars (plasmon position, particle concentration) and laser (wavelength, irradiation power and duration). The strong and broad plasmon spectrum of nanostars matches well the wavelength of the NIR laser. Within 5 minutes of laser irradiation, the temperature of 3 nM and 0.3 nM nanostars-containing solutions increased by 56 and 38° C., respectively, while $Na_3Cit$ buffer solution only increased by 18° C. Although the laser wavelength used in the study is beyond the range of tissue optical window due to the availability of the laser, the difference in temperature profile clearly indicates the photothermal transduction effect of nanostars. The photothermal ablation using nanostars was demonstrated on SKBR3 breast cancer cells.

Nonspecific cellular uptake of unlabeled nanostars showed a concentration dependent manner (data not shown). $Na_3Cit$-stabilized nanostars, when treated with FBS-containing media, resulted in passive adsorption of serum protein onto the particle surface. The non-specific interaction between serum proteins and cell membrane might facilitate the uptake of nanostars. Although nanostars were aggregated, the clustering might also increase the uptake. When combining a localized irradiation to cells accumulated with nanostars, a confined region of killing can be observed within 3 minutes, while laser irradiation or nanostars incubation alone generated no killing effect. With longer irradiation time, the photothermal ablation effect became more prominent. Unfortunately, due to higher water absorption at 980 nm, a small area of cells was non-specifically ablated after longer irradiation.

The photothermal response in vivo was demonstrated on an athymic nude mouse. Based on the ANSI regulation, the maximal permissible exposure to skin at 980 nm was 0.73 W/cm$^2$. Here, a power density of 0.56 W/cm$^2$ was applied to the area filled with nanostars in the subcutaneous layer. At this power density, a 12° C. of temperature increase was observed after 5 minutes of irradiation. Slight increase in injection area can be seen due to diffusion of nanoparticles. After the irradiation, a visible inflammation was noticed on the margin of the injection site probably as a result of thermal injury. In contrast, irradiating area of saline injection showed only 7° C. of temperature increase due to slightly high tissue absorption at 980 mn. Still no visible skin damage was seen. Further optimization to increase nanostars targeted binding, to improve nanostars stability in physiological environment, and to reduce non-specific laser heating would further enhance the selectivity and efficacy of photothermal killing. In this study, we employed gold nanostars as a new photothermal transducer for hyperthermic therapy. The nanostars synthesis is simple and quick. Based on theoretical calculations, at the plasmon peak nanostars exhibit an Abs/Sca cross section ratio greater than nanorods and nanoshells. In vitro, unlabeled nanostars locate predominately in the cytoplasm, as investigated by the two-photon photoluminescence imaging. The photothermal response was maximal when both NIR laser irradiation and nanoslars incubation were combined but only minimal when separated. The localized cell death intensified after longer irradiation suggesting a laser dose dependency. In vivo, a localized hyperthermia was achieved by irradiating an area containing subcutaneous injection of PEGylated nanostars but not saline. According to the methods of the present disclosure, size and plasmonic properties of nanostars can be optimized for photothermal response using laser in the tissue optical window.

Example 6

Silica-Coated Gold Nanostars for Combined SERS Detection and Photodynamic Treatment (PDT)

The synthesis of SERS-tagged gold nanostars coated with a silica shell encapsulating methylene blue (MB) is presented as a construct for combined PDT and SERS imaging. The surface plasmon band of the nanostars and the absorption band of the Raman reporter used fall within the NTR region. This is ideal for in vivo imaging since tissue absorption is minimal in this range, increasing the penetration depth of the excitation source and the efficiency of Raman scattering collection. Use of an excitation source that overlaps with the absorption of the Raman reporter allows for surface-enhanced resonance Raman scattering (SERRS), further enhancing the efficiency of Raman scattering by a few orders of magnitude. It is demonstrated herein that the core-shell particles with encapsulated MB show enhanced singlet oxygen generation as compared to core-shell particles grown without MB. Optical characterization of the nanocomposites was performed by Raman, fluorescence, and Vis-NIR absorption spectroscopies.

Materials.

Gold(111) chloride trihydrate ($HAuCl_4.3H_2O$), trisodium citrate dehydrate ($C_6H_5O_7Na_3.2H_2O$), 1N HCl, tetraethyl orthosilicate (TEOS), O-[2-(3-Mercaptopropionylamino)ethyl]-O'-methylpolyethylene glycol (mPEG-SH, MW 5 k), methylene blue hydrate (MB), 3,3'-Diethylthiatricarbocyanine iodide (OTIC), and methanol were purchased from Sigma-Aldrich at the highest purity grade available. Silver nitrate ($AgNO_3$, 99.995%) was supplied by Alfa Aesar. Pure-grade ethanol and $NH_4OH$ (29.5%) were obtained through VWR. Ultrapure water (18 MΩ cm-1) was used in all preparations. The Singlet Oxygen Sensor Green (SOSG) reagent was procured from Invitrogen.

Nanostar Synthesis.

Briefly, 12-nm gold seeds were synthesized by reduction of gold(III) with citrate. Nanostars were grown from the seed by reduction of gold(III) chloride with ascorbic acid in the presence of silver nitrate under acidic conditions. The stock concentration of particles is approximately 0.1 nM, as determined by Nanoparticle Tracking Analysis (NTA).

SERS-Tagging.

Freshly synthesized nanostars (10 mL) were capped with 5 μM mPEG-SH under gentle stirring for 15 minutes. The PEGylated particles were then centrifuged (10 k rcf, 15 minutes) twice at 4° C. to remove excess PEG and redispersed in water. To this solution, 5 μM DTTC in methanol was added and allowed to stir overnight. The DTTC-tagged particles were centrifuged (5 k rcf, 15 minutes) twice at 4° C. and resuspended into 2.3 mL of ethanol.

Methylene Blue Encapsulation by Silica Coating.

A modified Stober method was used for formation of the silica shell. Under gentle stirring, 2.25 mL of the nanostars in ethanol was added to a solution containing 2.0 mL of water and 6.8 mL ethanol. Methylene blue (final concentration 5 μM) in ethanol and 160 μL of NH$_4$OH were added to the mixture. Silica coating was initiated by the addition of 30 μL 10% TEOS in ethanol, and the reaction was allowed to proceed for three hours. The particles were then washed until no MB absorption could be detected from the supernatant (typically 2-3 times) at 4° C. by centrifugation (3.5 k rcf, 15 minutes) and redispersed into 5 mL of water.

Characterization.

Raman spectra with 785-nm excitation (25 m W) were recorded on a Jobin Yvon LabRAM ARAMIS system using a 1200-g mm-1 grating. Fluorescence and Raman spectra with 633-nm (8 mW, 10% laser power for fluorescence, 100% for Raman) excitation were recorded on a Renishaw inVia Raman microscope using an 1800-g mm-1 grating. Transmission electron microscopy (TEM) was performed on a FEI Tecnai G$^2$ Twin transmission electron microscope with an accelerating voltage of 160 kV. Vis-NIR spectra were acquired on a Shimadzu UV-3600. Particle concentrations were measured by NTA with a NanoSight NS500.

Singlet Oxygen Generation.

The fluorescent probe, SOSG, was used to indirectly measure singlet oxygen generation from the particles. On a 96-well plate, 90 μL of the coated particles were mixed with 10 μL of ~100 μM SOSG in methanol. The sample was excited using 63-nm laser light focused into the solution with a 10× objective. Laser power was 8 mW at the sample. Fluorescence intensity was measured with a BMG LABTECH FLUOstar Omega using an excitation filter of 500±10 nm and emission filter of 530±10 nm.

Figure 11:
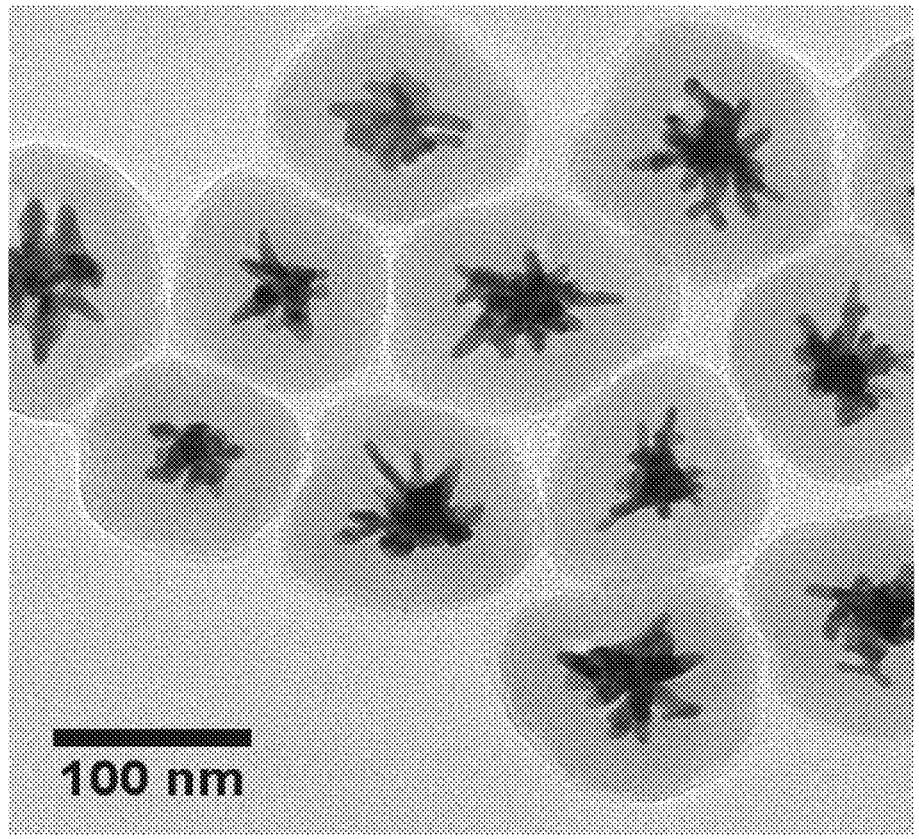
FIG. 11 is a TEM micrograph of the silica coated AuNS according to one or more embodiments of the present disclosure. The scale bar is 100 nm.
Figure 12:
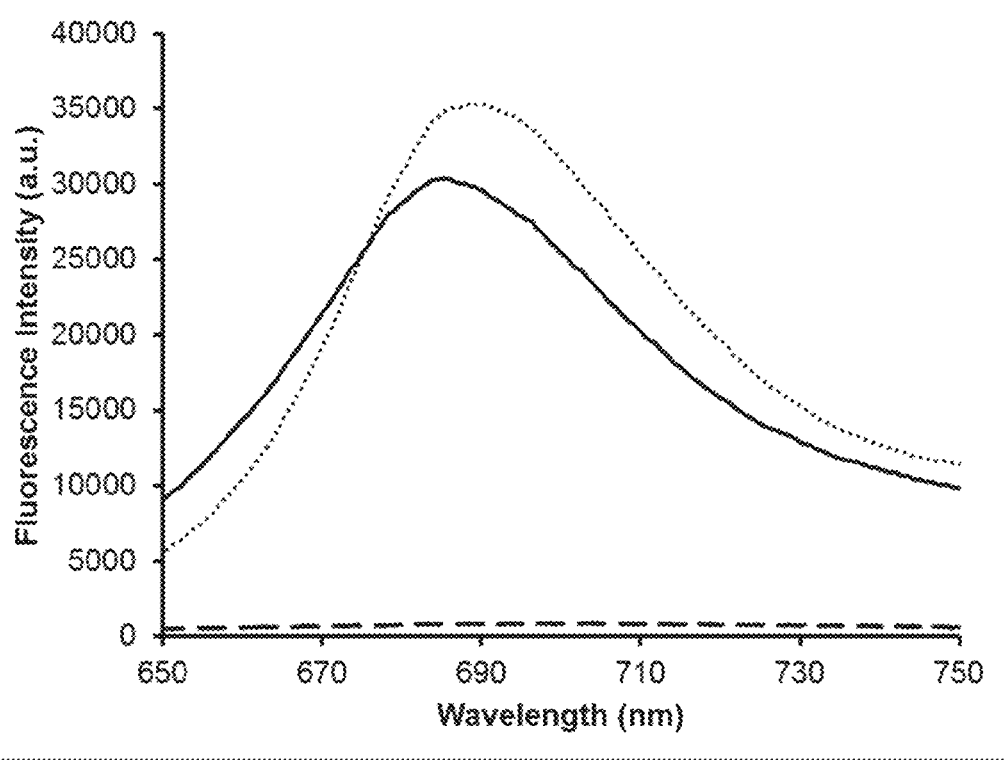
FIG. 12 is a fluorescence spectra of AuNS-DTTC@SiO$_2$-MB (solid line), MB-spiked AuNS-DTTC@SiO$_2$ (dotted line), and AuNS-DTTC@SiO$_2$ (dashed line) in water according to one or more embodiments of the present disclosure. Excitation was at 633 nm, 10 sec exposure time.

The use of PEG as a surfactant has been shown to increase the colloidal stability of gold nanoparticles enough to allow for redispersion into ethanol without aggregation. The PEG molecules have also been shown to be effective in facilitating the condensation of silica onto nanoparticles, creating a silica shell. Here PEG is utilized in silica coating to encapsulate MB in a mesoporous shell around gold nanostars of the present disclosure. Previous work has shown that MB is loaded into the silica matrix when present in solution during silica condensation using the Stober method. Unexpectedly, the capping of the gold nanostars of the present invention with PEG did not seem to interfere with the ability to tag them with the Raman reporter DTTC. It is presumed that the sulfur groups in the DTTC molecule aid in adsorption to the gold surface. Upon laser excitation at 785 nm, the DTTC-tagged particles showed no fluorescence signal, indicating that the dye is located at or near the gold surface, resulting in quenching. A strong SERRS signal was observed at 785 nm from silica encapsulated MB DTTC-tagged particles (AuNS-DTTC@SiO$_2$-MB), while the gold nanostars with silica encapsulated MB without DTTC (AuNS@SiO$_2$-MB) exhibited no appreciable signal (data not shown). Raman spectra of AuNS-DTTC @ SiO$_2$ particles without MB showed a much weaker signal when excited at 633 nm (data not shown). This is likely because the excitation is no longer resonant with the absorption band of DTTC or the Plasmon band of the nanostars. Silica coating of the AuNSs gave the expected red-shift in the Vis-NIR absorption spectrum due to an increase in the local refractive index around the nanoparticles. There appeared to be a small shoulder around 680 nm for the silica coated particles that may be attributed to the encapsulated MB. FIG. 11 shows a TEM image of the silica coated particles. Upon laser excitation at 633 nm, strong fluorescence is observed from the silica coated particles containing MB (FIG. 12). The AuNS-DTTC@SiO$_2$-MB show a blue shift of ~3 nm in the fluorescence spectrum compared to the AuNS-DTTC@SiO$_2$ sample spiked with 0.5 μM MB. Previous studies have suggested that caging and confinement effects of the silica matrix on an embedded dye can cause a blue shift in the fluorescence emission.

A centrifugation study was performed to examine the leaching behavior of MB from the silica matrix. Solutions of particles were acidified to pH 3 with HCl to limit the adsorption of MB onto the outer surface of the silica shell. The fluorescence emission of as-prepared AuNS-DTTC @SiO$_2$-MB was measured after varying numbers of washes using 633 nm excitation. For each wash, samples were centrifuged at 3.5 k rcf for 10 minutes, decanted, then redispersed in pH 3 water/HCl. The same measurements were performed on AuNS-DTTC@SiO$_2$ spiked with 0.5 μM MB, giving a similar initial fluorescence intensity as the AuNS-DTTC@SiO$_2$-MB (see FIG. 12). Measured intensity for the MB encapsulated and MB spiked particles was normalized by the initial intensity for each sample, respectively. It is shown that excessive washing can leech MB out of the silica matrix, although slower than MB adsorbed to the silica surface (data not shown).

Singlet oxygen generation from the particles was measured indirectly with the fluorescent probe, SOSG. Upon reaction with singlet oxygen, SOSG becomes fluorescent with excitation at a lamda max of 504 and emission at a lamda max of 525 nm. Singlet oxygen generation from AuNS-DTTC@SiO$_2$-MB was compared with AuNS-DTTC@SiO$_2$ (data not shown). The measured fluorescence intensities at each time point were nonnalized to the initial fluorescence of the sample. A significant increase in the amount of singlet oxygen generation was observed from the MB embedded particles.

Described above are SERS-tagged nanocomposites possessing a combined capability for SERS detection and singlet oxygen generation for PDT. This work has demonstrated the strong SERRS signal from DTTC-tagged nanostars at 785 nm laser excitation. Encapsulation of MB photosensitizing drug into a silica shell around the nanostars shows enhanced singlet oxygen generation upon laser excitation at 633 nm compared to silica coated nanostars without MB. These multimodal nanoprobes can be useful for therapeutic applications, diagnostics, and integrating SERS imaging and PDT.

Example 7

SERS of Nanostars

Monodisperse 50-nm gold nanostars (AuNSs) were synthesized according to the method described in Example 1, which were easily labeled with SERS active dyes without the need for removal of surface polymer on the nanoparticles. Spherical silver (AgNPs) and gold (AuNPs) nanoparticles of roughly 50-nm in diameter were also prepared. For spherical silver nanoparticles, because both standard citrate and hydroxylamine reduction methods produced a wide size distribution. Seed-mediated methods of synthesis were utilized to create monodisperse 50-nm AgNPs. This AgNP, however, was sensitive to oxidation; SERS dyes addition to a 3-day old AgNP sample had much less SERS intensity than the fresh-made AgNP. Because of this, all AgNP studied were prepared fresh. For spherical gold nanoparticles (AuNPs), the modified Turkevich citrate reduction method produced slightly oval-shaped, monodisperse 50-nm AuNPs. Both gold nanostars and spheres did not show significant oxidation effect.

Figure 13:
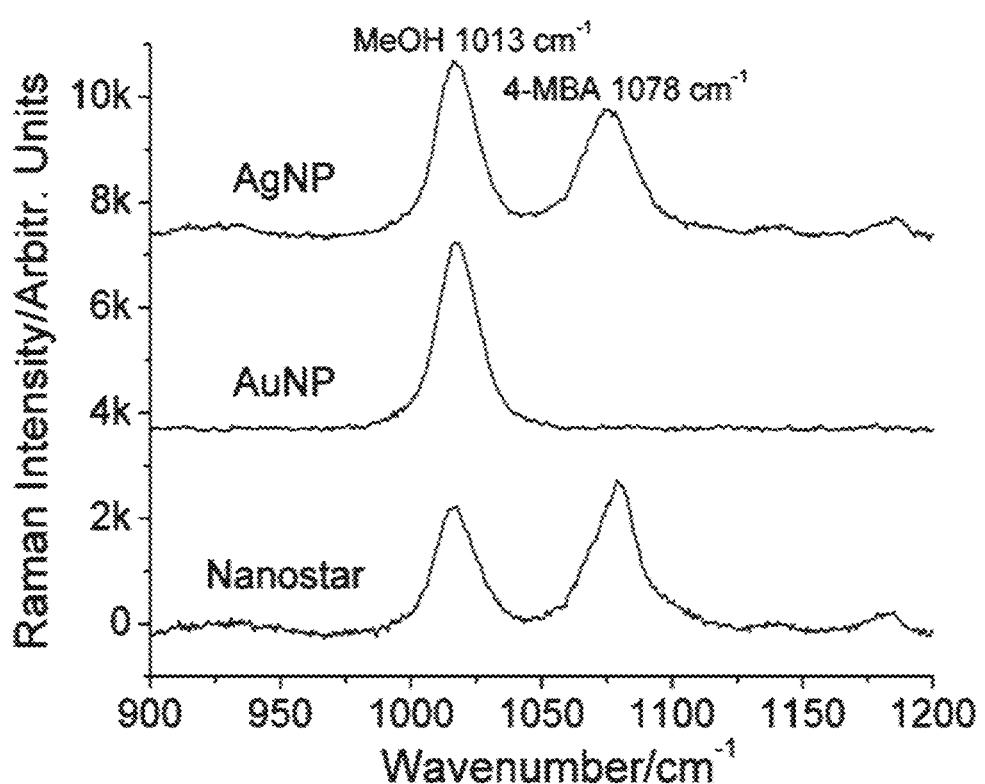
FIG. 13 is a SERS spectra (baseline subtracted) of 1 μM 4-MBA in 0.1 nM AgNP, AuNP, and nanostar solutions examined through a Raman microscope under 785 nm excitation according to one or more embodiments of the present disclosure. Methanol (10% v/v) was used as an internal reference. Wavenumber 1013 and 1078 represents Raman signals from MeOH and 4-MBA, respectively.

The extinction spectrum maximum of the three different nanoparticles ranges from 400-800 nm based on their composition and geometry (FIG. 13). Previously, it has been shown on simulation that nanostars' plasmon peak and intensity are determined by the branch aspect ratio and branch number/length, respectively. Because of the heterogeneous branch morphology, nanostar ensembles probably enable a wider range of LSPR modes, which explains the broadening of the extinction spectra. Upon the addition of 1 µM 4-MBA, which has less than the full surface coverage (20~40%) on nanoparticles and did not induce apparent aggregation, a slight spectral red-shift was observed. The plasmon red-shifted more on AgNP (4 nm) than on AuNP (1 nm); this probably reflects the different thiol binding efficiency between silver (59 kcal/mol) and gold (45 kcal/mol). For nanostars, even though their branches contain a small amount of silver, enhanced thiol binding does not explain the red-shift difference between nanostars (15 nm) and AgNP (4 nm). A previous report found on simulation a remarkable plasmon red-shift on nanostars when the surrounding refractive index increases. It is therefore very likely that the plasmon from the branches is more sensitive to the refractive index change than the plasmon from the spheres, hence a significant plasmon red-shift on nanostars.

FIG. 13 shows the non-resonance SERS comparison of nanostars, AgNP and AuNP, with the most prominent peaks being the Stokes features appearing at 1013 $cm^{-1}$ and 1078 $cm^{-1}$, which are assigned to the C—O stretching mode of MeOH and ring breathing mode of the 4-MBA. It is noteworthy that no NaCl was added to avoid nanoparticle aggregation. Although there was no strong evidence of aggregation on UVVIS, nanoparticle tracking analysis still showed a small amount of larger particles on all samples after the addition of 4-MBA.

Because adding 4-MBA generated the smallest size change when compared to adding 4-aminothiophenol, thiophenol, and 4-methylbenzinethiol, it is believed that nanoparticle ensembles labeled with 4-MBA were the closest to their non-aggregated state. This allows for SERS measurement to reflect the realistic EM enhancement on nanoparticle ensembles. Although this is not a single particle SERS study, the ensemble-averaged signal still provides crucial information for SERS comparison between different compositions and geometries. At 785 nm, nanostars exhibited a slightly greater enhancement than AgNP but significantly outperformed AuNP (data not shown). The EF of isolated AuNP was not visible in our setup; an EF of lower than 4 orders of magnitude on isolated AuNP was previously reported. Nanostars, with the presence of multiple hot spots on the branches, have at least comparable EF to AgNP, which is typically 2 to 3 orders of magnitude stronger than AuNP. Being able to achieve a similar EF to AgNP without the toxicity of silver, nanostars are particularly advantageous due to the superior biocompatibility of gold. Moreover, because aggregation is generally hard to control and irreproducible, the advantage of having strong SERS without the need to form aggregates make gold nanostars a useful SERS contrast agent.

Figure 14:
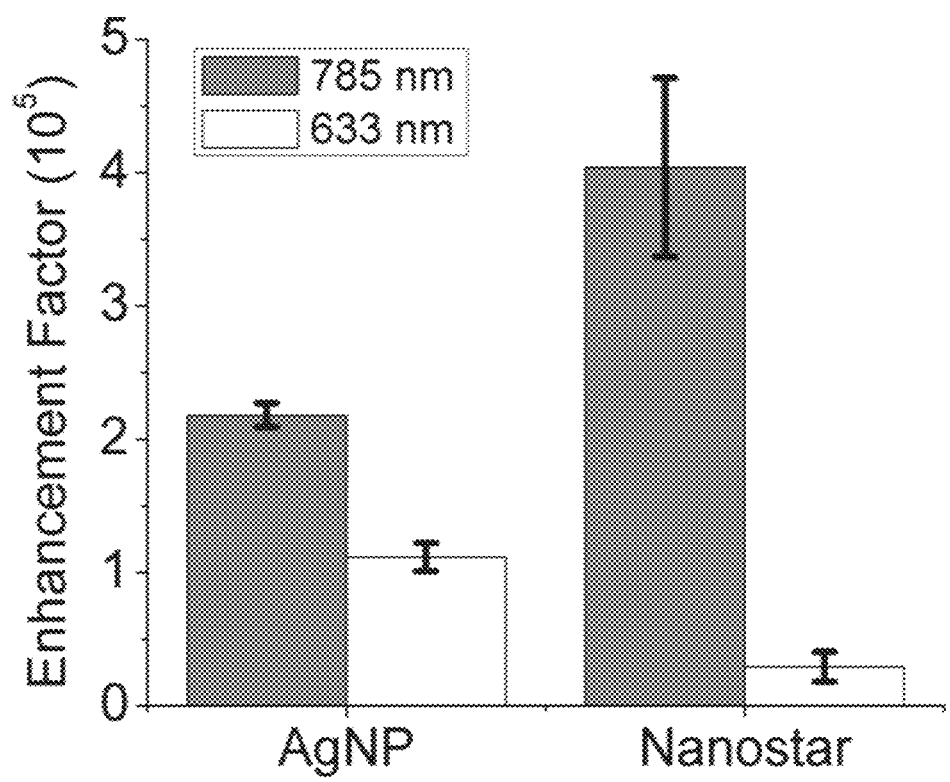
FIG. 14 is a graph showing enhancement factors of AgNP and nanostar under 785 nm (grey) and 633 nm (white) laser excitation according to one or more embodiments of the present disclosure. AuNP was omitted due to no 4-MBA SERS signal available for EF calculation. Error bar is 1 SD.

FIG. 14 illustrates a laser wavelength dependence of SERS EF on both AgNP and nanostars. Generally, maximal enhancement occurs at excitation near the LSPR maximum. With AgNP, which has a plasmon maximum located near 405 nm, a 2-fold stronger EF was obtained from 785 nm than 633 nm excitation, suggesting a possible minute aggregation dominating the overall SERS response. Such aggregation was barely detectable under UVVIS but was only slightly visible under Nanosight. On nanostars, more than 10-fold stronger EF was observed under excitation from 785 nm than from 633 nm. Stronger SERS response has previously been reported under 785 nm than at shorter wavelength. Under 633 nm excitation, the ensemble-averaged nanostars SERS EF ($0.3 \times 10^5$) is lower than previously reported ($2-5.7 \times 10^5$), probably due to different dyes/nanostars concentrations or NaCl used.

Under 785 nm excitation, the ensemble-averaged nanostars SERS EF is around $4 \times 10^5$, which is slightly higher than previous results of ($1 \times 10^5$) and ($2-5 \times 10^3$). Having sharper branches and no polymer coating on the nanostars provided herein might contribute the slight EF improvement. However, it is noteworthy that the calculated SERS EF decreases with increasing analyte concentrations (data not shown). At lower analyte concentrations it is likely that most analyte molecules attach to the outermost part of the nanostars (i.e. the tip) where the strongest EM field locates. At higher analyte concentration, molecules may also bind to inner regions (e.g. the shaft, trough); the higher EM enhancement at the tips is then averaged out by fields from the shaft or other regions. Such phenomenon is more apparent under 785 nm excitation, which is in resonance with the branch plasmon. Therefore, a near 10-fold stronger EF was found at the lower concentration than the higher one. This is in agreement with the "lightning rod" effect demonstrating the role of branch tip as hot spot. Without wishing to be bound by any particular theory of mechanism, in short, a combination of LSPR matching the excitation laser and presence of multiple hot spots on nanostars may explain their strong SERS enhancement.

However, although nano stars have slightly higher EF than gold nanorod ensembles ($10^4$-$10^5$), its EF is still lower than that from gold dimers ($10^7$-$10^8$) or clustered patterns ($10^8$-$10^{10}$). With more branches per nanoparticle, it is reasonable that nanostars have several fold higher enhancement than nanorods. However, the EF from sharp protrusion may be less than from a coupled configuration. Dimers, despite their higher EF, remain difficult to fabricate uniformly. Film-based clustered patterns cannot be applied easily to biological systems as well. Although nanostars coupled to a gold film produced SERS EF of $10^{10}$, enhancement that high could not be reached even upon NaCl induced aggregation in solution.

It is noteworthy that the ensemble-averaged SERS increment upon aggregation was much less profound from nanostars than from spheres. Instead of a branch facing another branch, aggregated nanostars probably have branches collapsing into each other, hence breaking the hot spots on the branches. It is likely that nanostar aggregates produce much less EM enhancement than sphere aggregates due to the possible plasmon deactivation from interaction between tips with different geometry and orientation. Although aggregates may produce strong SERS, keep in mind that the reproducible formation of, as well as access to, hotspots in nanoparticle dimers or aggregates is limited. Controlled aggregation in ensemble is appealing but still remains a difficult task with various yields. In contrast, nanostars possess a high EF as non-aggregated monodisperse entities, and therefore do not suffer from the non-linear enhancement effect due to aggregation. Until a more reliable method is developed for the formation of reproducible and accessible hot spots, nanostars may nonetheless be one of the most sensitive and controllable SERS platforms in solution.

To fabricate a strong SERS probe for bioapplications, several dyes were investigated. Non-thiolated dyes (e.g. rhodamine, crystal violet) were found unable to remain on the nanoparticle surface during the silica coating process. Thiolated, thiocyanated, thionine dyes, such as 4-MBA, fluorescein isothiocyanate, methylene blue, all sustained the silica coating process but the resulting SERS signal under 785 nm excitation remains insufficient, requiring long integration time for adequate signal-to-noise ratio. One exception is 3,3'-diethylthiatricarbocyanine iodide (DTTC), which is a NIR dye that has two cyanine groups that will facilitate its anchoring onto the gold surface. DTTC is also resonant with the 785 nm excitation laser, creating a stronger resonance Raman for use in SERS detection. Upon silica coating, the hydrodynamic size of the SERS probes used in this study were around 110 nm (data not shown).

Figure 15:
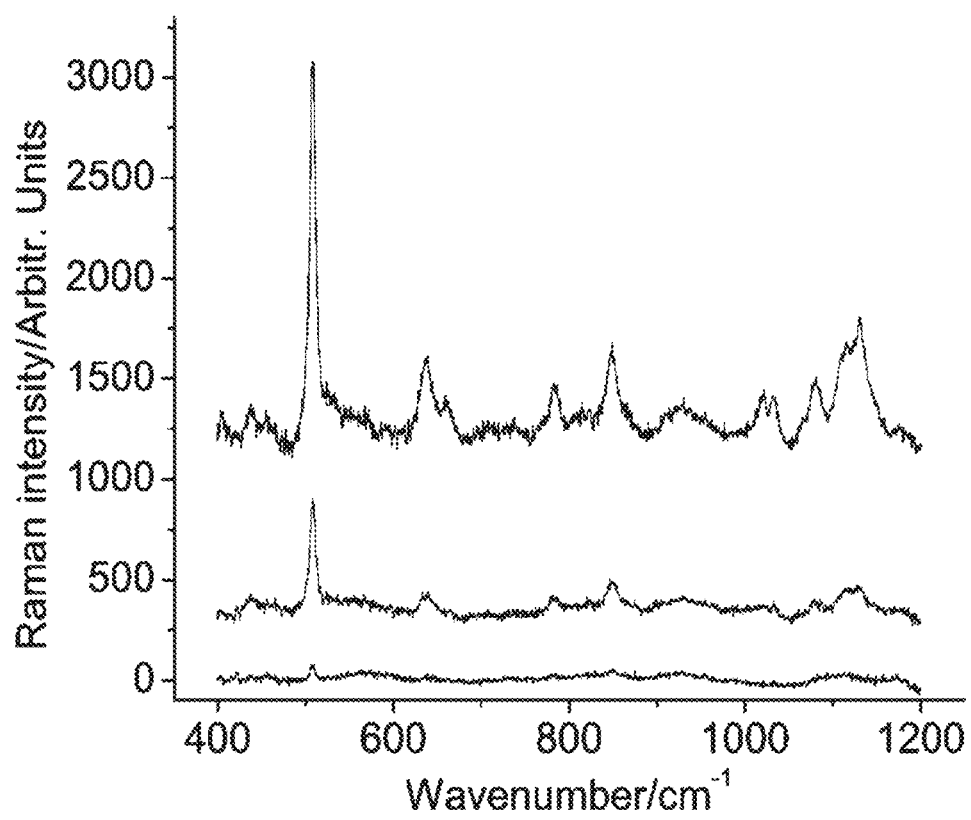
FIG. 15 shows three SERS spectra (baseline subtracted) of different intracellular regions (top SERS spectrum: cytoplasm; middle SERS spectrum: nucleus; bottom SERS spectrum: glass) on BT549 cells incubated 24 hrs with silica-coated nanostars labeled with a SERS dye (DTTC) according to one or more embodiments of the present disclosure.

FIG. 15 shows the SERS spectra of silica-coated DTTC-encoded SERS probe in different compartments of cells with short integration time (10 sec). Similar strategies have been applied for SERS mapping in cells or tissues previously. In our study, two-photon microscopy disclosed that SERS probes were accumulated mostly in the cytoplasm with minimal intranuclear accumulation after 24 hours of probe incubation (FIG. 15). SERS signals were found to be the greatest in the cytoplasm region but remained one-fifth as strong in the nuclear region. The discrepancy between the two-photon image (minimal intranuclear nanostars) and SERS spectra could be the fact that due to a low axial resolution (from the large axial optical probe volume), the SERS spectra collected in the nuclear region may be confounded by signals from the cytoplasm above or underneath the nucleus. Further use of multifunctional SERS probes by incorporating other modalities (e.g. photodynamic therapy, photothermal therapy, MRI contrast) may bring forth promises for molecular imaging and cancer therapy.

Chemicals.

Gold (III) chloride trihydrate ($HAuCl_4$), sodium citrate tribasic dihydrate ($Na_3Cit$), L(+)-ascorbic acid (AA), silver nitrate ($AgNO_3$), hydrochloric acid (HCl), O[2-(3-mercaptopropionylamino)ethyl]-O'-methylpolyethylene glycol ($M_w$ 5,000; $SHPEG_{5k}$), 4-mercaptobenzoic acid (4-MBA), ethanol (EtOH), methanol (MeOH), tetraethyl orthosilicate (TEOS), 3,3'-diethylthiatricarbocyanine iodide (DTTC) were purchased from Sigma-Aldrich (St. Louis, Mo.). All chemicals were used as received. Millipore Synergy ultra-pure water (DI) of resistivity=18.2 MΩ cm was used in all aqueous solutions. All glassware and stir bars were cleaned with aqua regia solution and oven-dried before use. (Caution: aqua regia is extremely dangerous. Please use it with extra caution.)

Gold Seed Synthesis.

Gold seeds were made by adding 15 ml of 1% (w/v) $Na_3Cit$ solution into 100 ml of boiling 1 mM $HAuCl_4$ solution under vigorous stirring. After 30 min, the solution was cooled, filtered by a 0.22 μm nitrocellulose membrane, and kept at 4° C. for long-term storage.

Gold Spheres (50 nm) Synthesis.

Gold spheres were made by adding 0.8 ml of 1% (w/v) $Na_3Cit$ solution into 100 ml of boiling 0.25 mM $HAuCl_4$ solution under vigorous stirring. After 30 min, the solution was cooled, filtered by a 0.22 μm nitrocellulose membrane and stored at 4° C. for long-term storage. Before use, the solution underwent centrifugal wash (3000×g for 15 min) once and was resuspended to 0.1 nM.

Silver Spheres (50 nm) Synthesis.

Silver spheres were synthesized using a seed-mediated method modified from the nanostars synthesis method below. In 10 ml of 100 mM $AgNO_3$ solution, 100 μl of the citrate gold seed solution was added under room temperature. Immediately afterwards, a mixture of 50 μl of 100 mM AA and 10 μl of HCl was administered. One hour later, the solution underwent centrifugal wash (3000×g for 15 min) once and was resuspended to 0.1 nM. The Ag spheres were used within a day to reduce the detrimental effect from surface oxidation.

Nanostars Synthesis.

Gold nanostars were synthesized using a seed-mediated method. Detailed synthesis and characterization of the nanostars has been presented elsewhere. Briefly, in 10 ml 0.25 mM $HAuCl_4$ solution, 10 μl of 1N HCl and 12 nm citrate gold seeds 100 μl were added followed by the simultaneous addition of 100 μl $AgNO_3$ and 50 μl 100 mM AA under stirring (700 rpm). The reaction was performed under room temperature, and the process is completed in less than a minute. Afterwards, the solution underwent centrifugation wash (3000×g 15 min) once, resuspended to 0.1 nM, and kept under 4° C. for long-term storage.

Structural and Optical Characterization.

Transmission electronic microscopy (TEM; Fei Tecnai $G^2$ Twin, 200 kV) was used for structural analysis. The particle hydrodynamic size distribution, concentration, and ζ-potential were determined by nanoparticle tracking analysis (NTA 2.1; build 0342) using NanoSight NS500 (Nanosight Ltd. UK). A UV-VIS spectrophotometer (Shimadzu UV-3600; Shimadzu corporation, Japan) was used to collect the extinction spectrum.

SERS Measurements and Instrumentation.

100 μl of freshly prepared 4-MBA (10 μM in 10% MeOH) was mixed with 1 ml particles solutions for 10 min. All particle solutions were pre-diluted to 0.1 nM particle concentrations before adding the 4-MBA. Special care was taken to avoid particle aggregation. The 4-MBA Raman spectrum from each particle solution was collected using a Renishaw InVia Raman system (633 nm HeNe laser, 8 mW, 1800 gr/mm grating; Renishaw Inc. IL) or a Jobin Yvon Horiba LabRam ARAMIS (785 nm diode-laser, 40 mW, 1200 gr/mm grating; Horiba Scientific, NJ) (FIG. 51 (Supporting information)). Three samples were collected for each experimental condition.

Examining the Enhancement Factor.

The SERS EF of a nanoparticle ensemble is determined by the ratio of SERS cross-section ($\sigma_{4MBA:SERS}$) to normal Raman cross-section ($\sigma_{4MBA:Raman}$) of 4-MBA in nanoparticle and normal solution, respectively $$\left( EF = \frac{\sigma_{4MBA:SERS}}{\sigma_{4MBA:Raman}} \right).$$

4-MBA was chosen because 1) it has a thiol group that strongly binds to the metal surface; 2) it does not fluoresce at 633 nm or 785 nm; and 3) the carboxyl groups maintain the negative surface charge at pH 7 in order to reduce particle aggregation. Also, ensembles in solution are less aggregated than dried solid phase. This allowed us to study the effect of particle geometry on SERS without the non-linear interference from aggregation. Usually, the EF is calculated by $$EF = \frac{\sigma_{4MBA:SERS}}{\sigma_{4MBA:Raman}} = \frac{I_{4MBA:SERS} \times C_{4MBA:Raman}}{I_{4MBA:Raman} \times C_{4MBA:SERS}}.$$

However, because these three types of nanoparticles have uneven surface area (e.g. oval shape, branches), the exact number of surface-bound 4-MBA (especially those located at the hot spot) cannot be simply estimated. Also, due to an overlapping absorption background to the Raman emission spectra, the SERS intensity needs to be normalized by an internal reference. To solve these issues, we selected a 4-MBA concentration of sub-total surface coverage per particle. Because all 4-MBA molecules would attach to the nanoparticle through the strong dative bond, the amount of 4-MBA added can be assumed as the amount of 4-MBA on the nanoparticle surface. Also, we added a small amount (5~10% v/v) of MeOH, which does not induce aggregation and is not enhanced by the nanoparticle, as an internal reference. The next step is to obtain $\sigma_{4MBA:SERS}$ and $\sigma_{4MBA:Raman}$.

The $\sigma_{4MBA:SERS}$ is calculated in reference to $\sigma_{MeOH:Raman}$ using the equation $$\sigma_{4MBA:SERS} = \frac{I_{4MBA:SERS} \times C_{MeOH:SERS}}{C_{4MBA:SERS} \times I_{MeOH:SERS}} \times \sigma_{MeOH:SERS}$$

$$\sigma_{4MBA-SERS} = \frac{I_{4MBA-SERS} \times C_{MeOH-SERS}}{C_{4MBA-SERS} \times I_{MeOH-SERS}} \times \sigma_{MeOH-Raman},$$

where $C_{4MBA:SERS}/C_{MeOH:SERS}$ and $I_{4MBA:SERS}/I_{MeOH:SERS}$ are the concentrations and SERS intensities of 4-MBA and MeOH in nanoparticle solution. The SERS intensity was defined by the area under curve, which was calculated by fitting the spectrum using the pseudo-Voigt function in OriginPro 8 (OriginLab Corporation, USA). Raman intensities of 4-MBA and MeOH were measured using the aromatic ring vibration (1078 cm$^{-1}$) and the C—O stretch vibration (1016 cm$^{-1}$), respectively. Because the two vibration bands were in close proximity, the background absorption from the solution would be similar on both bands. The same strategy can be applied to obtaining $\sigma_{4MBA:Raman}$.

To obtain $\sigma_{4MBA:Raman}$, 4-MBA was dissolved to 10-50 mM in NaOH 1 N and 2% (v/v) MeOH. The average $\sigma_{4MBA:Raman}$ measured were calculated 9.23×10$^{-30}$ and 2.75×10$^{-30}$ cm$^2$/molecule at 633 nm and 785 nm, respectively. The $\sigma_{MeOH:Raman}$ was calculated from multiple mixing ratios of MeOH and acetonitrile. MeOH's C—O stretch vibration (1016 cm$^{-1}$) and acetonitrile's C—C stretch vibration (919 cm$^{-1}$) were used for calculation. $\sigma_{MeOH:Raman}$ at both 633 nm (0.693×10$^{-30}$ cm$^2$/molecule) and 785 nm (0.207×10$^{-30}$ cm$^2$/molecule) were determined in reference to acetonitrile's cross-section extrapolated from the known value. The final step is $$EF = \frac{\sigma_{4MBA:SERS}}{\sigma_{4MBA:Raman}} = \frac{\frac{I_{4MBA:SERS} \times C_{MeOH:SERS}}{C_{4MBA:SERS} : I_{MeOH:SERS}} \times \sigma_{MeOH:SERS}}{\frac{I_{4MBA:Raman} \times C_{MeOH:Raman}}{C_{4MBA:Raman} \times I_{MeOH:Raman}} \times \sigma_{MeOH:Raman}}.$$

SERS Dye Encoding and Silica-Encapsulation on Nanostars.

Freshly synthesized nanostars (10 mL) were capped with 5 μM SHPEG$_{5k}$ under gentle stirring for 15 min. The PEGylated particles were then centrifuged (10000×g) twice at 4° C. to remove excess PEG and redispersed in DI. DTTC (5 μM) in methanol was added to this solution and allowed to stir overnight. The DTTC-tagged particles were centrifuged (5000×g) twice at 4° C. to remove excess DTTC and resuspended in 2.3 mL of EtOH. A modified Stöber method was then used for formation of the silica shell. Under gentle stirring, 2.25 mL of the nanostars in ethanol was added to a solution containing 2.0 mL of water and 6.8 mL of EtOH followed by the addition of 160 μL of NH$_4$OH. Silica coating was initiated by the addition of 30 μL of 10% TEOS in EtOH, and the reaction was allowed to proceed for 3 h. The nanoparticles were then centrifugally purified (3500×g) twice and redispersed into 5 mL DI.

Example 8

Multiplex of Nanostars

A facile synthesis is reported herein of bovine serum albumin (BSA)-protected NIR-SERRS probes. Due to the intrinsically narrow Raman peaks, spectral fitting of the entire fingerprint allows accurate quantification of each SERRS probe where quantitative multiplexing of 4 NIR-SERRS probes was achieved with sample solutions (in vitro), and then through excised chicken skins (ex vivo) to mimic the experimental conditions of subcutaneous detection in animal.

Figure 16A:
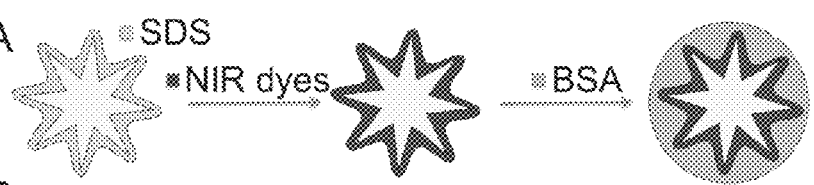
FIGS. 16A-16B show A) a schematic diagram of NIR-SERRS probe synthesis and B) a baseline-subtracted SERS spectra from probes made of 4 different NIR dyes (785 nm excitation, 100 mW, 100 ms) according to one or more embodiments of the present disclosure.
Figure 16B:
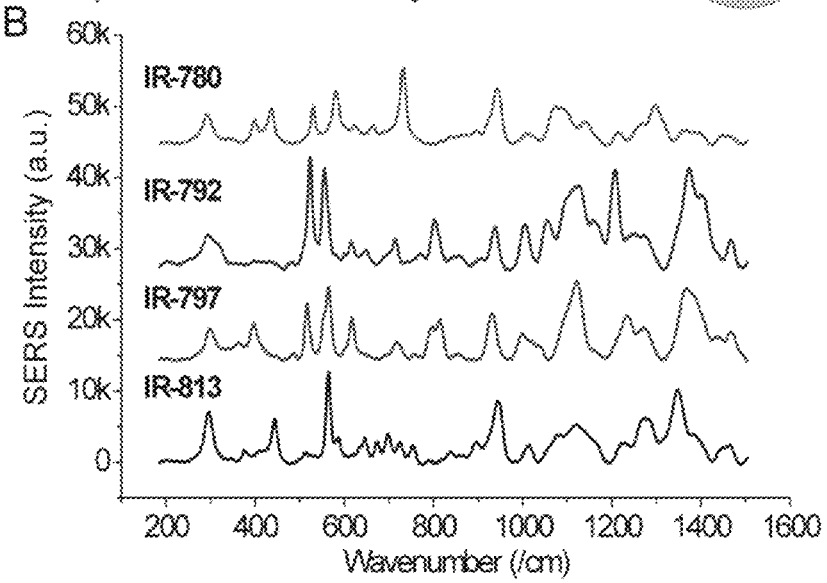

FIG. 16A illustrates the schematics of NIR-SERRS probes fabrication. The gold NS were prepared based on the method disclosed herein at Example 1, but with the addition of 0.02% sodium dodecyl sulfate (SDS. Sigma Aldrich), which formed a bilayer (ca. 3~4 nm) on top of the gold surface to stabilize nanoparticles and to ensure their isolated state upon the addition of hydrophobic NIR dyes. Without SDS, a small amount (e.g. 10 nM) of NIR dyes can destabilize the gold surface causing early aggregation. The presence of SDS not only can stabilize the nanoparticle but also can facilitate the adsorption of positively-charged hydrophobic NIR dyes (e.g. IR-780, IR-792, IR-797, IR-813; Sigma Aldrich) onto the metal nanostar surface, hence generating strong SERRS intensity upon dye addition (FIG. 16B). Furthermore, SDS coated on the anisotropic star-shape, instead of a spherical shape, may entrap more dyes onto the NS surface. In contrast, negatively-charged NIR dyes (e.g. IR-725, IR-783; Sigma Aldrich) showed only fluorescence background. A similar response but of lower SERRS intensity was also observed on NS coated with poly(sodium 4-styrenesulfonate) (MW 70,000; Sigma-Aldrich). It is possible that the sulfonate groups of the SDS help to attract positive dyes but keep the negative dyes away from the metal surface; the alkyl chains of the SDS may also help to adsorb the hydrophobic dyes. Combining SDS-facilitated dye adsorption with both dyes and nanoparticles' plasmon resonating with the excitation NIR laser, the SERRS responses from these SDS-coated NIR dye-labeled NS were several orders greater than those made from non-resonant dyes or isolated spherical nanoparticles.

Nanostars of different plasmon peak positions were investigated for the highest SERRS response. It is generally regarded that the best excitation is located a little blue-shifted with respect to the plasmon maximum. For NIR responsive NS of broad plasmon, however, the best excitation may shift towards the opposite direction. It is noteworthy that matching the excitation with the plasmon peak may induce strong surface plasmon resonance but suffer from SERS signal loss from the background absorption. Such absorption in the Stoke shift region (800-900 nm) for 785-nm excited NIR-SERRS probes has detrimental effect on the absolute SERRS intensity. By investigating nanostars with plasmon peak below, at, and above the excitation wavelength, it was observed that the less the absorption in the 800-900 nm range the stronger the absolutely SERRS intensity.

To achieve biocompatibility and physiological stability, bovine serum albumin (BSA) 0.2% (w/v) was added to the above solutions. BSA and PEG have been exploited for enhancing the biocompatibility of nanoparticles for many bioapplications. In our study, BSA was chosen rather than PEG due to its ability to protect the NS from reshaping and aggregation in PBS. Positively charged BSA may adsorb onto the sulfonate layer or anchor onto the gold metal surface via the cysteine residues on the BSA in order to provide steric protection of NS. BSA also helps to encapsulate the NIR-SERRS probes in order to prevent leaching of the NIR dyes. The BSA-protected SERRS probes can remain SERS-active for at least two weeks.

Quantitative SERRS multiplex detection was first performed using liquid samples in vials (in vitro) then through excised chicken skins (ex vivo). Previously, in vivo multiplexing has been achieved by simple peak measurement or multivariate spectral fitting. Both methods lack the power to decompose complex Raman spectra and to identify the signal fraction of each probe from the mixture; both methods are not suitable for analyzing NIR-SERRS spectra, which typically contain strong fluorescence background and complex overlapping peaks. To quantitatively decompose complex SERRS spectra without fluorescence subtraction, a spectral decomposition method was applied reported by Lutz et al. that was based on the least-square regression using 4 reference spectra and a free fitting polynomial (data not shown). Such a method is rapid and easy to implement; it offers satisfactory fitting results. For in vitro multiplexing, the analytical SERRS signal fractions obtained were in good agreement with the predetermined SERRS probe mixing ratios (data not shown). The spectral decomposition can be achieved in a wide range of concentrations under a short collection time due to high signal-to-noise ratio (SNR) from the NIR-SERRS probes.

For ex vivo multiplexing, the SERRS spectra were examined through several layers of chicken skin to mimic the subcutaneous detection in animal. A single layer of skin produces 95% (98% for 2 layers) of signal reduction, which originates primarily from the tissue scattering and the simplistic optical setup (data not shown). To acquire SERRS spectra with sufficient SNR, data was collected with higher laser power and longer integration. An additional spectrum from the chicken skin alone was added as reference. The quantitative ex vivo SERRS multiplexing was performed using 4 SERRS probes (IR-780, IR-792, IR-797, and IR-813). Data were collected under 785 nm excitation (400 mW, 10 sec, 3 averages). The resulting signal fraction was close to the predetermined ratio but not as good as the in vitro ones. This was to be expected due to the lower SNR value of the SERS signal detected through the chicken skin. Higher irradiation energy was employed but resulted in heating up the SERRS probe; such phenomenon is favorable for photothermal therapy but the higher temperature would increase the rate of dye leaching from the metal surface hence more fluorescence background.

In this study, plasmonic gold NS were used to fabricate strong NIR-SERRS probes for in vitro and ex vivo multiplex detection for the first time. Having both the nanoparticles and dyes in the NIR region together with the unique SDS-coated star-shape geometry to entrap more dye produced SERRS signals several orders of magnitude more intense than those with non-resonant dyes or spherical counterparts. Even though a strong fluorescence background is always present in SERRS, quantitative multiplexing can still be achieved with high precision with in vitro samples and, in a lesser extent, with ex vivo tissue samples.

In another experiment, SERS spectra of 4-MBA (1 µM) on 0.1 nM nanospheres (FIG. 17A) and nanostars (FIG. 17B) were examined under 785 nm and 633 nm excitations.

10% v/v methanol was used as an internal reference. Table 3 below shows the measured probe ratios on multiplexing of 4 SERS probes.

Table 3 below shows the measured probe ratios on multiplexing of 4 SERS probes.

| Probe name | Probe ratio (DTNB:4ATP:FITC:4MBA) | | |
|---|---|---|---|
| | 1:1:0:0 | 0:0:1:1 | 1:1:1:1 |
| DTNB | 0.4497 | 0 | 0.1835 |
| 4ATP | 0.3767 | 0.0006 | 0.1642 |
| FITC | 0.022 | 0.3344 | 0.2021 |
| 4MBA | 0.0067 | 0.3503 | 0.2116 |
| Blank | 0.0183 | 0 | 0 |
| Measured probe ratio | 1:0.84:0.05:0.01 | 0:0.002:1:1.05 | 1:0.89:1.10:1.15 |

DTNB: 5,5'-dithiobis-2-nitrobenzoic acid,
4ATP: 4-aminothiophenol,
FITC: Fluorescein isothiocyanate,
4MBA: 4-mercaptobenzoic acid,
Blank: nanostars solution alone Example 9

Applications in Flow Cytometry

Over the years flow cytometry has had a dramatic effect on many different fields of research, including biomedical diagnostics and prognosis. It can be described as the automated analysis of optical properties of individual cells, either live of fixed, in a fluidic system [P. Kasili and T. Vo-Dinh, "Hyperspectral Imaging System Using Acousto-Optic Tunable Filter for Flow Cytometry Applications", Cytometry, 69A(8):835-841 (2006)]. Based on the molecular probes used, flow cytometry provides specific fluorescence and light scatter signals emitted by the cells being analyzed. Flow cytometry usually measures two broad categories of information: whole cell fluorescence and light scatter. Whole cell fluorescence measures intracellular concentrations of proteins while, light scatter signals provides data about inclusion body formation. This information is valuable in process optimization because it provides a clear correlation between fluorescence intensity and the presence or absence of target proteins. In addition to these broad categories of information, flow cytometry offers the capability of analysis of multiple parameters, some of which are measured simultaneously for each cell such as low-angle forward scatter intensity, approximately proportional to cell diameter; orthogonal (90 degree) scatter intensity, approximately proportional to the quantity of granular structures within the cell; and fluorescence intensities at several wavelengths. Therefore, flow cytometry permits the acquisition of multiple optical properties, which can be effectively recorded for every individual cell via the quantification of fluorescence intensities.

There is a great interest in using alternative detection methods, such as Raman and SERS in flow cytometry. Raman and SERS detection methods allow multiplex detection using a multispectral or hyperspectral imaging (HSI) detection system. The major components of the HSI system include a 2-D intensified charge-coupled device (ICCD) detector, an acousto-optic tunable filter (AOTF) or a liquid crystal tunable fileter (LCTF) device, excitation laser source, excitation and emission optics, and a laptop for data acquisition and processing. An AOTF is a rapid wavelength-scanning solid-state device, which operates as a tunable optical band pass filter, having no moving parts and can be scanned at very high rates (microsecond time scale). This device allows an investigator to rapidly record an image at various wavelengths. AOTFs are solid-state optical band-pass filters that can be tuned to various wavelengths within microseconds by varying the frequency of the acoustic wave propagating through the medium. The solid-state nature of an AOTF includes a high-throughput (~70-90% diffraction efficiency) dispersive element with no moving parts, thus increasing the ruggedness of the instrumentation. Since AOTFs with high spatial resolution and large optical apertures are available, they can be applied for spectral imaging applications. Moreover, they facilitate the dual acquisition of spatial and spectral features of a range of fluorescent colors that are representative of cellular properties. Thus, based on the application characteristics of the AOTF, HSI has the potential to provide for spectroscopic information and optical imaging measurement when coupled to flow cytometry. Spectroscopic analysis is generally used to obtain an entire spectrum of a single sample site within a wavelength region of interest. On the other hand, optical imaging methods record a two-dimensional (2-D) image of an area of the sample of interest at one specific wavelength. Thus, HSI combines these two measurement modalities and allows the recording of the entire emission for every pixel on the entire image in the field of view and the signal at wavelength intervals within a given spectral range in addition to the multiparameter analysis offered by flow cytometry.

Measurement System.

Figure 18:
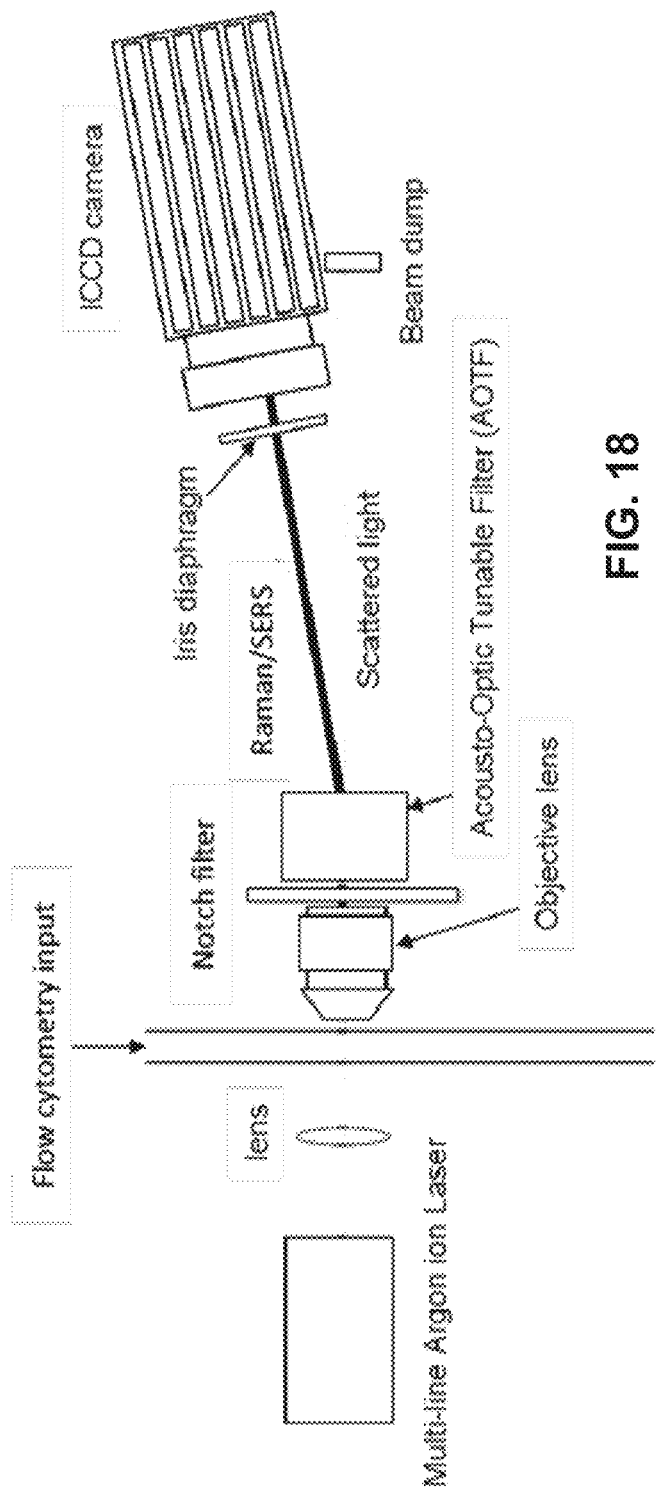
FIG. 18 is a diagram of a SERS Multispectral detection and Hyperspectral imaging system for flow cytometry according to one or more embodiments of the present disclosure.

FIG. 18 shows the principal components of the HSI system that can be adapted to flow cytometry applications. Its principal components include, the excitation source a 25 mW multi-line argon ion laser (Melles Griot, Carlsbad, Calif.) that features either multi-line output (up to six wavelengths simultaneously) or single-wavelength with the use of the prism wavelength selector providing a wavelength range from 454.5 nm to 528.7 nm (488 nm and 514 nm are the most intense lines); an objective lens, AOTF Model TEAF5-0.3-1.3 (Brimrose Corporation of America, Baltimore, Md.) and ICCD detector Model PI-Max512-t18/G/II (Roper Scientific, Trenton, N.J.) operated at −20° C. The ICCD was controlled with Winspec software, provided by Roper Scientific while the RF generator used (Brimrose-model AT) was controlled by a DOS-based computer using a 16-b computer controller board supplied by Brimrose. Custom allows control the AOTF, supporting various scanning modes and fixed-frequency operation. FIG. 18 shows a schematic representation of the operating principle of an AOTF. This device consists of a piezoelectric transducer bonded to a birefringent crystal. The transducer is exited by a radio frequency (RF) (50-200 MHz) and generates acoustic waves in a birefringent crystal. These pressure waves establish a periodic modulation of the index of refraction of the crystal via the elasto-optic effect. As an applied acoustic wave propagates through the crystal, it creates a grating by alternately compressing and relaxing the lattice. Those density changes create periodic index of refraction changes that act collectively like a transmission diffraction grating; except for the fact that only one wavelength is diffracted at a time. As a result, the AOTF behaves as a tunable filter. The wavelength of the diffracted beam is varied by changing the frequency of the acoustic wave, thereby also adjusting the grating spacing. This is the basis of an electronically tuned optical filter, which operates via Bragg diffraction of light by periodic modulations in the index of refraction in the crystal established by the acoustic waves. The Bragg grating diffracts only light that enters the crystal within an angle normal to the face of the crystal. This range is called the acceptance angle of the AOTF. The percentage of light diffracted is the diffraction efficiency of the device. This parameter greatly depends on the incidence angle, the wavelength selected, and the power of the RF signal. For visible wavelengths in a tellurium oxide crystal (the diffraction medium of the AOTF), the applied acoustic wave is RF and can be switched very quickly (typically in less than 50 µs) compared to other technologies. In a typical AOTF, the first-order diffracted beam is separated from the undiffracted beam (i.e., the zero-order beam) by diffraction. The undiffracted beam exits the crystal at the same angle as the incident light beam, while the diffracted beam exits the AOTF at a small angle (6°) with respect to the incident beam. An ICCD detector is placed at a distance so that the diffracted light can be monitored, while the undiffracted light does not irradiate the detector. The interface to the computer was accomplished via an RS232 connection system.

Any patents or publications mentioned in this specification are indicative of the levels of those skilled in the art to which the present disclosure pertains. These patents and publications are herein incorporated by reference in their entirety to the same extent as if each individual publication was specifically and individually indicated to be incorporated by reference.

One skilled in the art will readily appreciate that the present disclosure is well adapted to carry out the objects and obtain the ends and advantages mentioned, as well as those inherent therein. The present examples along with the methods described herein are presently representative of preferred embodiments, are exemplary, and are not intended as limitations on the scope of the invention. Changes therein and other uses will occur to those skilled in the art which are encompassed within the spirit of the present disclosure as defined by the scope of the claims.

What is claimed is:

1. A superparamagnetic plasmonics-active gold nanostar resulting from a process comprising:
    reducing aqueous gold ($Au^{3+}$) to solid gold (Au) onto citrate-stabilized gold seeds in an acidic solution, wherein the citrate-stabilized gold seeds comprise superparamagnetic iron oxide particles coated with a layer of gold; and
    mixing a silver salt compound with a weak reducing agent into the solution under conditions such that the superparamagnetic plasmonics-active gold nanostars are produced.

2. The gold nanostar of claim 1, wherein the $Au^{3+}$ comprises tetrachloroauric acid ($HAuCl_4$).

3. The gold nanostar of claim 1, wherein the weak reducing agent consists essentially of ascorbic acid.

4. The gold nanostar of claim 1, wherein the silver salt compound consists essentially of silver nitrate ($AgNO_3$).

5. The gold nanostar of claim 2, wherein the weak reducing agent consists essentially of ascorbic acid, and wherein the ratio of the ascorbic acid to the $HAuCl_4$ ranges from about 1.5 to about 2.

6. The gold nanostar of claim 1, wherein a size of the nanostar is less than about 100 nm.

7. The gold nanostar of claim 1, wherein the concentration of a silver cation of the silver compound ranges from about 5 µM to about 30 µM and a plasmon peak of the nanostar ranges from about 600 nm to about 1000 nm.

8. The gold nanostar of claim 1, wherein the nanostar further comprises one or more of an optical label, a photosensitizer, and a photoactivator.

9. The gold nanostar of claim 8, wherein the optical label comprises one or more of a fluorescence label, fluorescein, fluorescein isothiocyanate (FITC), thionine dyes, rhodamine, crystal violet, Raman label, 3,3'-diethylthiatricarbocyanine iodide (DTTC), absorbance label, positively-charged hydrophobic NIR dyes, IR-780, IR-792, IR-797, IR-813, methylene blue hydrate (MB), 4-mercaptobenzoic acid (4-MBA), 5,5'-dithiobis-2-nitrobenzoic acid (DTNB), and 4-aminothiophenol (4ATP).

10. The gold nanostar of claim 8, wherein the nanostar comprises one or both of a layer surrounding the nanostar having within the layer the one or more of the optical label, the photosensitizer, and the photoactivator, and a protective overlayer surrounding the layer.

\* \* \* \* \*